(12) United States Patent
Beeson et al.

(10) Patent No.: US 7,649,009 B2
(45) Date of Patent: Jan. 19, 2010

(54) PYRAZOLE AMIDE DERIVATIVES, COMPOSITIONS CONTAINING SUCH COMPOUNDS AND METHODS OF USE

(75) Inventors: Teresa Beeson, Princeton, NJ (US); Linda Brockunier, Orange, NJ (US); Emma R. Parmee, Scotch Plains, NJ (US); Subharekha Raghavan, Teaneck, NJ (US)

(73) Assignee: Merck & Co., Inc., Rahway, NJ (US)

( * ) Notice: Subject to any disclaimer, the term of this patent is extended or adjusted under 35 U.S.C. 154(b) by 495 days.

(21) Appl. No.: 11/631,580

(22) PCT Filed: Jul. 1, 2005

(86) PCT No.: PCT/US2005/023684

§ 371 (c)(1),
(2), (4) Date: Jan. 4, 2007

(87) PCT Pub. No.: WO2006/017055

PCT Pub. Date: Feb. 16, 2006

(65) Prior Publication Data

US 2007/0203186 A1    Aug. 30, 2007

Related U.S. Application Data

(60) Provisional application No. 60/586,047, filed on Jul. 7, 2004.

(51) Int. Cl.
*A61K 31/4155* (2006.01)
*C07D 231/10* (2006.01)
*C07D 401/06* (2006.01)

(52) U.S. Cl. .......... 514/406; 548/250; 548/254; 548/356.1; 548/373.1; 548/374.1; 546/184; 546/192; 546/207; 546/268.1; 546/275.4; 514/315; 514/317; 514/403

(58) Field of Classification Search .......... 514/403, 514/406, 315, 317; 548/250, 254, 356.1, 548/373.1, 374.1; 546/184, 192, 207, 268.1, 546/275.4
See application file for complete search history.

(56) References Cited

U.S. PATENT DOCUMENTS

| | | | |
|---|---|---|---|
| 5,776,954 | A | 7/1998 | de Laszlo et al. |
| 6,174,901 | B1 | 1/2001 | Mantlo et al. |
| 6,218,431 | B1 | 4/2001 | Schoen et al. |
| 6,613,942 | B1 | 9/2003 | Ling et al. |
| 6,881,746 | B2 | 4/2005 | Lau et al. |
| 6,953,812 | B2 | 10/2005 | Jorgensen et al. |
| 2003/0203946 | A1 | 10/2003 | Behrens et al. |
| 2005/0203108 | A1 | 9/2005 | Lau et al. |

FOREIGN PATENT DOCUMENTS

| | | |
|---|---|---|
| WO | WO 97/01551 | 1/1997 |
| WO | WO 98/21957 | 5/1998 |
| WO | WO 98/22108 | 5/1998 |
| WO | WO 98/22109 | 5/1998 |
| WO | WO 00/36088 | 6/2000 |
| WO | WO 01/38325 | 5/2001 |
| WO | WO 02/40444 A1 | 5/2002 |
| WO | WO 03/051357 A1 | 6/2003 |
| WO | WO 2004/050039 | 6/2004 |
| WO | WO 2004/069158 A2 | 8/2004 |

*Primary Examiner*—Golam M Shameem
(74) *Attorney, Agent, or Firm*—Richard C. Billups; Catherine D. Fitch

(57) ABSTRACT

Pyrazole amides are disclosed. The compounds are useful for treating type 2 diabetes and related conditions. Pharmaceutical compositions and methods of treatment are also included.

23 Claims, No Drawings

PYRAZOLE AMIDE DERIVATIVES, COMPOSITIONS CONTAINING SUCH COMPOUNDS AND METHODS OF USE

CROSS REFERENCE TO RELATED APPLICATIONS

This is a US National Phase application based upon PCT Application Serial No. PCT/US2005/023684 filed on Jul. 1, 2005, which was based upon Provisional Application Ser. No. 60/586,047 filed on Jul. 7, 2004, priority of which is claimed hereunder.

BACKGROUND OF THE INVENTION

The present invention relates to pyrazole amide derivatives, compositions containing such compounds and various methods of treating or preventing type 2 diabetes mellitus and related conditions.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level >126 mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure >130/80 mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by (alpha cells in pancreatic islets in response to failing blood glucose levels, The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly. In addition to elevated levels of circulating insulin, type 2 diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

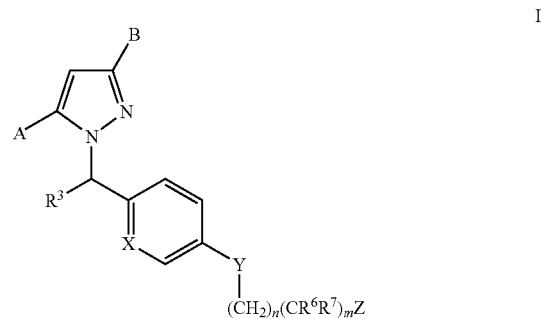

I or a pharmaceutically acceptable salt or solvate thereof, wherein:

Y represents —C(O)—N($R^5$)— or —O—;

one of A and B represents —C(O)—NH—R and the other represents

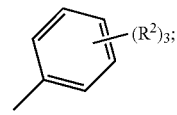

$R^1$ represents H or is independently selected from the group consisting of:
a) $C_{1-16}$alkyl optionally substituted with:
  (1) 1-5 halo groups up to a perhaloalkyl group;
  (2) 1 oxo group;
  (3) 1-2 OH groups;
  (4) 1-2 $C_{1-10}$alkoxy groups, each optionally substituted with: up to five halo or a perhaloalkoxy, 1 OH or $CO_2R^a$ group;
  (5) 1 $CO_2R^a$ or $S(O)_pR^d$;
  (6) 1-2 Aryl, Hetcy or HAR groups, each optionally substituted as follows:
    (a) 1-5 halo groups,
    (b) 1 OH, $CO_2R^a$, CN, $S(O)_pR^d$, $NO_2$ or $C(O)NR^bR^c$,
    (c) 1-2 $C_{1-10}$alkyl or alkoxy groups, each optionally substituted with: 1-5 halo, up to perhaloalkyl, and 1-2 OH or $CO_2R^a$ groups; and
    (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups;
b) Aryl, HAR, Hetcy, each optionally substituted as set forth below:
  (1) 1-3 $C_{1-10}$alkyl or alkoxy groups optionally substituted as follows: 1-5 halo groups; 1-2 OH groups; $CO_2R^a$; CN; $S(O)_pR^d$; phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and (2) phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups;

said Aryl, HAR, Hetcy group b) being further optionally substituted on carbon by a group selected from the group consisting of;

(3) 1-5 halo groups;
(4) 1-2 OH groups;
(5) 1 $S(O)_pR^d$, $NO_2$ or CN group;
(6) 1-2 $CO_2R^a$;
(7) —$C(O)NR_bR^c$;

each $R^2$ is H or is selected from the group consisting of:
(a) halo, OH, $CO_2R^a$, CN, $SO_pR^d$, $NO_2$,
(b) $C_{1-6}$alkyl or $OC_{1-6}$alkyl optionally substituted with: (1) 1-5 halo groups up to a perhaloalkyl group; (2) $CO_2R^a$ CN, $S(O)_pR^d$ or OH; (3) phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups;

$R^3$ is H or $C_{1-3}$alkyl;
$R^5$ is H or $C_{1-6}$alkyl;
$R^6$ is selected from the group consisting of H, OH, F and $C_{1-3}$alkyl;
$R^7$ is H or F, or $R^6$ and $R^7$ are taken in combination and represent oxo;
$R^a$ is H or $C_{1-10}$alkyl, optionally substituted with phenyl, OH, $OC_{1-6}$alkyl, $CO_2H$, $CO_2C_{1-6}$alkyl and 1-3 halo groups;
$R^b$ is H or $C_{1-10}$alkyl;
$R^c$ is H or is independently selected from:
(a) $C_{1-10}$alkyl, optionally substituted with OH, $OC_{1-6}$alkyl, $CO_2H$, $CO_2C_{1-6}$alkyl, and 1-3 halo groups;
(b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
(c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and
(d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;
$R^d$ is $C_{1-10}$alkyl, Aryl or Ar—$C_{1-10}$alkyl;
m is an integer selected from 0, 1 and 2;
n is an integer selected from 0 to 6;
p is an integer selected from 0, 1 and 2, and
when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl) and
X is CH or N.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and teat-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. Examples of cycloalkyl include cyclopropyl, cyclobutyl, cyclopentyl, cyclohexyl, cycloheptyl, decahydronaphthyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and 0, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine.

In its broadest aspect, the invention relates to a compound represented by formula I:

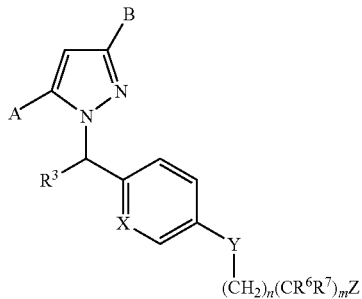

or a pharmaceutically acceptable salt or solvate thereof, wherein:

Y represents —C(O)—N($R^5$)— or —O—;

one of A and B represents —C(O)—NH—R and the other represents

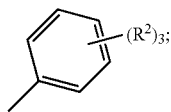

$R^1$ represents H or is independently selected from the group consisting of:
a) C-$_{1-16}$alkyl optionally substituted with:
  (1) 1-5 halo groups up to a perhaloalkyl group;
  (2) 1 oxo group;
  (3) 1-2 OH groups;
  (4) 1-2 C$_{1-10}$alkoxy groups, each optionally substituted with: up to five halo or a perhaloalkoxy, 1 OH or CO$_2$R$^a$ group;
  (5) 1 CO$_2$R$^a$ or S(O)$_p$R$^d$;
  (6) 1-2 Aryl, Hetcy or HAR groups, each optionally substituted as follows:
    (a) 1-5 halo groups,
    (b) 1 OH, CO$_2$R$^a$, CN, S(O)$_p$R$^d$, NO$_2$ or C(O)NR$^b$R$^c$,
    (c) 1-2 C$_{1-10}$alkyl or alkoxy groups, each optionally substituted with: 1-5 halo, up to perhaloalkyl, and 1-2 OH or CO$_2$R$^a$ groups; and
  (d) 1-2 phenyl rings, each of which is optionally substituted as follows: 1-5 halo groups up to perhalo, 1-3 C$_{1-10}$alkyl or alkoxy groups, each being further optionally substituted with 1-5 halo up to perhalo, or 1-2 hydroxy or CO$_2$R$^a$ groups;
b) Aryl, HAR, Hetcy, each optionally substituted as set forth below:
  (1) 1-3 C$_{1-10}$alkyl or alkoxy groups optionally substituted as follows: 1-5 halo groups; 1-2 OH groups; CO$_2$R$^a$; CN; S(O)$_p$R$^d$; phenyl optionally substituted as follows: (i) 1-5 halo groups, (ii) 1 CO$_2$R$^a$, CN, S(O)$_p$R$^d$, NO$_2$ or C(O)NR$^b$R$^c$ group, (iii) 1-2 C$_{1-10}$alkyl or alkoxy groups, each optionally substituted with: 1-5 halo, up to perhaloalkyl, and 1-2 OH or CO$_2$R$^a$ groups;; and
  (2) phenyl optionally substituted as follows: (i) 1-5 halo groups, (ii) 1 CO$_2$R$^a$, CN, S(O)$_p$R$^d$, NO$_2$ or C(O)NR$^b$R$^c$ group, (iii) 1-2 C$_{1-10}$alkyl or alkoxy groups, each optionally substituted with: 1-5 halo, up to perhaloalkyl, and 1-2 OH or CO$_2$R$^a$ groups;

said Aryl, HAR, Hetcy group b) being further optionally substituted on carbon by a group selected from the group consisting of;
  (3) 1-5 halo groups;
  (4) 1-2 OH groups;
  (5) 1 S(O)$_p$R$^d$, NO$_2$ or CN group;
  (6) 1-2 CO$_2$R$^a$;
  (7) —C(O)NR$^b$R$^c$;

each $R^2$ is H or is selected from the group consisting of:
  (a) halo, OH, CO$_2$R$^a$, CN, SO$_p$R$^d$, NO$_2$,
  (b) C$_{1-6}$alkyl or OC$_{1-6}$alkyl optionally substituted with:
  (1) 1-5 halo groups up to a perhaloalkyl group; (2) CO$_2$R$^a$ CN, S(O)$_p$R$^d$ or OH; (3) phenyl optionally substituted as follows: (i) 1-5 halo groups, (ii) 1 CO$_2$R$^a$, CN, S(O)$_p$R$^d$, NO$_2$ or C(O)NR$^b$R$^c$ group, (iii) 1-2 C$_{1-10}$alkyl or alkoxy groups, each optionally substituted with: 1-5 halo, up to perhaloalkyl, and 1-2 OH or CO$_2$R$^a$ groups;

$R^3$ is H or C$_{1-3}$alkyl;

$R^5$ is H or C$_{1-6}$alkyl;

$R^6$ is selected from the group consisting of H, OH, F and C$_{1-3}$alkyl;

$R^7$ is H or F, or $R^6$ and $R^7$ are taken in combination and represent oxo;

$R^a$ is H or C$_{1-10}$alkyl, optionally substituted with phenyl, OH, OC$_{1-6}$alkyl, CO$_2$H, CO$_2$C$_{1-6}$alkyl and 1-3 halo groups;

$R^b$ is H or C$_{1-10}$alkyl;

$R^c$ is H or is independently selected from:
  (a) C$_{1-10}$alkyl, optionally substituted with OH, OC$_{1-6}$alkyl, CO$_2$H, CO$_2$C$_{1-6}$alkyl, and 1-3 halo groups;
  (b) Aryl or Ar—C$_{1-6}$alkyl, each optionally substituted with 1-5 halos and 1-3 members selected from the group consisting of: CN, OH, C$_{1-10}$alkyl and OC$_{1-10}$alkyl, said alkyl and alkoxy being further optionally substituted with 1-5 halo groups up to perhalo;
  (c) Hetcy or Hetcy-C$_{1-6}$alkyl, optionally substituted with 1-5 halo groups and 1-3 groups selected from: oxo, C$_{1-10}$alkyl and OC$_{1-10}$alkyl, said alkyl and alkoxy being further optionally substituted with 1-5 halo groups up to perhalo; and
  (d) HAR or HAR-C$_{1-6}$alkyl, optionally substituted with 1-5 halo groups and 1-3 groups selected from: C$_{1-10}$alkyl and OC$_{1-10}$alkyl, said alkyl and alkoxy being further optionally substituted with 1-5 halo groups up to perhalo;

$R^d$ is C$_{1-10}$alkyl, Aryl or Ar—C$_{1-10}$alkyl;

m is an integer selected from 0, 1 and 2;

n is an integer selected from 0 to 6;

p is an integer selected from 0, 1 and 2, and when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl) and X is CH or N.

An aspect of the invention that is of interest relates to a compound represented by formula I or a pharmaceutically acceptable salt or solvate thereof, wherein:

Y represents —C(O)—N($R^5$)— or —O—;
one of A and B represents —C(O)—NH—R and the other represents

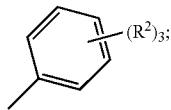

$R^1$ represents H or is independently selected from the group consisting of:
a) $C_{1-10}$alkyl optionally substituted with:
  (1) 1-3 halo groups;
  (2) 1 oxo group;
  (3) 1 OH groups;
  (4) 1-2 $C_{1-4}$alkoxy groups, each optionally substituted with: up to three halo groups;
  (5) 1 $CO_2R^a$ or $S(O)_pR^d$;
  (6) 1 Aryl, Hetcy or HAR group, optionally substituted as follows:
    (a) 1-3 halo groups,
    (b) 1 $CO_2R^a$, CN, $S(O)_pR^d$, $NO_2$ or $C(O)NR^bR^c$,
    (c) 1-$C_{1-6}$alkyl or alkoxy group, each optionally substituted with: 1-3 halo groups; and
    (d) 1 phenyl ring, optionally substituted as follows: 1-3 halo groups, 1-2 $C_{1-3}$alkyl or alkoxy groups, each being further optionally substituted with 1-3 halo groups;
b) Aryl, HAR, Hetcy, each optionally substituted as set forth below:
  (1) 1-2 $C_{1-6}$alkyl or alkoxy groups optionally substituted as follows: 1-3 halo groups; OH, $CO_2R^a$; CN; $S(O)_pR^d$; phenyl optionally substituted as follows: (i) 1-3 halo groups, (ii) 1 $CO_2R^a$, CN, $S(O)_pR^d$, $NO_2$ or $C(O)NR^bR^c$ group, (iii) 1-2 $C_{1-6}$alkyl or alkoxy groups, each optionally substituted with: 1-3 halo, and 1-2 OH or $CO_2R^a$ groups;; and
  (2) phenyl optionally substituted as follows: (i) 1-3 halo groups, (ii) 1 $CO_2R^a$, CN, $S(O)_pR^d$, $NO_2$ or $C(O)NR^bR^c$ group, (iii) 1-2 $C_{1-6}$alkyl or alkoxy groups, each optionally substituted with: 1-3 halo groups;

said Aryl, HAR, Hetcy group b) being further optionally substituted on carbon by a group selected from the group consisting of;
  (3) 1-3 halo groups;
  (4) 1 OH, $S(O)_pR^d$, $NO_2$, CN, $CO_2R^a$ or —$C(O)NR^bR^c$ group;
    each $R^2$ is H or is selected from the group consisting of:
    (a) halo, $CO_2R^a$, CN, $SO_pR^d$, $NO_2$,
    (b) $C_{1-6}$alkyl or $OC_{1-6}$alkyl optionally substituted with:
      (1) 1-3 halo groups up to a perhaloalkyl group; (2) $CO_2R^a$ CN, $S(O)_pR^d$ or OH; (3) phenyl optionally substituted as follows: (i) 1-3 halo groups, (ii) 1 $CO_2R^a$, CN, $S(O)_pR^d$, $NO_2$ or $C(O)NR^bR^c$ group, (iii) 1-2 $C_{1-6}$alkyl or alkoxy groups, each optionally substituted with: 1-5 halo groups;
$R^3$ and $R^5$ are H or $C_{1-3}$alkyl;
$R^6$ is selected from the group consisting of H, OH, F and $C_{1-3}$alkyl;
$R^7$ is H or F;
$R^a$ is H or $C_{1-6}$alkyl, optionally substituted with phenyl, OH, $OC_{1-4}$ alkyl, $CO_2H$, $CO_2C_{1-6}$alkyl and 1-3 halo groups;
$R^b$ is H or $C_{1-3}$alkyl;
$R^c$ is H or is independently selected from:
  (a) $C_{1-6}$alkyl, optionally substituted with OH, $OC_{1-4}$alkyl, $CO_2H$, $CO_2C_{1-6}$alkyl, and 1-3 halo groups;
  (b) Aryl or Ar—$C_{1-6}$alkyl, each optionally substituted with 1-3 halos and 1 member selected from the group consisting of: CN, OH, $C_{1-6}$alkyl and $OC_{1-6}$alkyl, said alkyl and alkoxy being further optionally substituted with 1-3 halo groups up to perhalo;
  (c) Hetcy or Hetcy-$C_{1-6}$alkyl, optionally substituted with 1-3 halo groups and 1 group selected from: oxo, $C_{1-6}$alkyl and $OC_{1-6}$alkyl, said alkyl and alkoxy being further optionally substituted with 1-3 halo groups up to perhalo; and
  (d) HAR or HAR-$C_{1-6}$alkyl, optionally substituted with 1-5 halo groups and 1 group selected from: $C_{1-6}$alkyl and $OC_{1-6}$alkyl, said alkyl and alkoxy being further optionally substituted with 1-3 halo groups up to perhalo;
$R^d$ is $C_{1-6}$alkyl, Aryl or Ar—$C_{1-6}$alkyl;
m is an integer selected from 0, 1 and 2;
n is an integer selected from 0 to 6;
p is an integer selected from 0, 1 and 2, and
when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl) and
X is CH or N.

Another aspect of the invention that is of interest relates to compounds of formula I wherein Y represents —C(O)—$NR^5$—. Within this aspect of the invention, all other variables are as originally defined with respect to formula I.

Another aspect of the invention that is of interest relates to compounds of formula I wherein Y represents —C(O)—$NR^5$— and $R^5$ represents H. Within this aspect of the invention, all other variables are as originally defined with respect to formula I.

Another aspect of the invention that is of interest relates to compounds of formula I wherein Y represents O. Within this aspect of the invention, all other variables are as originally defined with respect to formula I.

Another aspect of the invention that is of interest relates to compounds of formula I wherein A represents —C(O)NH—$R^1$. Within this aspect of the invention, all other variables are as originally defined with respect to formula I.

Another aspect of the invention that is of interest relates to compounds of formula I wherein B represents —C(O)NH—$R^1$. Within this aspect of the invention, all other variables are as originally defined with respect to formula I.

Another aspect of the invention that is of interest relates to compounds of formula I wherein $R^1$ is selected from the group consisting of: H, $C_{1-10}$alkyl and aryl. Within this aspect of the invention, all other variables are as originally defined with respect to formula I.

Another aspect of the invention that is of interest relates to compounds of formula I wherein A represents —C(O)NH—$R^1$ and $R^1$ represents $C_{1-10}$alkyl or phenyl optionally substituted with $C_{1-6}$alkyl, $OC_{1-6}$alkyl, halo $C_{1-6}$alkyl and halo $C_{1-6}$alkoxy. Within this aspect of the invention, all other variables are as originally defined with respect to formula I.

Another aspect of the invention that is of interest relates to compounds of formula I wherein each $R^2$ is independently selected from the group consisting of: H, halo, $C_{1-6}$alkyl, $OC_{1-6}$alkyl and $C_{1-6}$alkyl or $OC_{1-6}$alkyl substituted with 1-3 halo groups. Within this aspect of the invention, all other variables are as originally defined with respect to formula I.

Another aspect of the invention that is of interest relates to compounds of formula I wherein $R^3$ represents H. Within this aspect of the invention, all other variables are as originally defined with respect to formula I.

Another aspect of the invention that is of interest relates to compounds of formula I wherein X represents CH. Within this aspect of the invention, all other variables are as originally defined with respect to formula I.

Another aspect of the invention that is of interest relates to compounds of formula I wherein n and m represent 0, 1 or 2, such that the sum of m and n is 0, 1, 2 or 3. Within this aspect of the invention, all other variables are as originally defined with respect to formula I.

Another aspect of the invention that is of interest relates to compounds of formula I wherein Z represents tetrazole or $CO_2H$. Within this aspect of the invention, all other variables are as originally defined with respect to formula I.

An aspect of the invention that is of particular interest relates to compounds of formula I wherein:

X represents CH;

Y represents —C(O)—NH—;

A represents —C(O)NH—$R^1$ wherein $R^1$ represents a member selected from the group consisting of: H, $C_{1-10}$alkyl, aryl-$C_{1-10}$alkyl or phenyl optionally substituted with one of $C_{1-6}$alkyl, $OC_{1-6}$alkyl, halo $C_{1-6}$alkyl and halo $C_{1-6}$alkoxy;

B represents

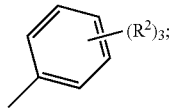

each $R^2$ is independently selected from the group consisting of: H, halo, $C_{1-6}$alkyl, $OC_{1-6}$alkyl and $C_{1-6}$alkyl or $OC_{1-6}$alkyl substituted with 1-3 halo groups;

$R^3$ represents H;

n and m represent 0, 1 or 2, such that the sum of m and n is 0, 1, 2 or 3 and

Z represents tetrazole or $CO_2H$.

Species that are of particular interest are shown in the examples provided herein.

Another aspect of the invention that is of interest relates to a pharmaceutical composition comprising a compound as described above with respect to formula I in combination with a pharmaceutically acceptable carrier.

Another aspect of the invention that is of interest relates to a method of treating type 2 diabetes mellitus in a mammalian patient in need of such treatment comprising administering to said patient a compound as described above with respect to formula I in an amount that is effective to treat type 2 diabetes mellitus.

Another aspect of the invention that is of interest relates to a method of delaying the onset of type 2 diabetes mellitus in a maimmalian patient in need thereof, comprising administering to the patient a compound as described above in accordance with formula I in an amount that is effective to delay the onset of type 2 diabetes mellitus.

Another aspect of the invention that is of interest relates to a method of treating hyperglycemia, diabetes or insulin resistance in a mammalian patient in need of such treatment which comprises administering to said patient a compound as described above in accordance with formula I in an amount that is effective to treat hyperglycemia, diabetes or insulin resistance.

Another aspect of the invention that is of interest relates to a method of treating non-insulin dependent diabetes mellitus in a mammalian patient in need of such treatment comprising administering to the patient an anti-diabetic effective amount of a compound in accordance with formula I as described above.

Another aspect of the invention that is of interest relates to a method of treating obesity in a mammalian patient in need of such treatment comprising administering to said patient a compound in accordance with formula I as described above in an amount that is effective to treat obesity.

Another aspect of the invention that is of interest relates to a method of treating Syndrome X in a mammalian patient in need of such treatment, comprising administering to said patient a compound in accordance with formula I as described above in an amount that is effective to treat Syndrome X.

Another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound as described above with respect to formula I in an amount that is effective to treat said lipid disorder.

Another aspect of the invention that is of interest relates to a method of treating atherosclerosis in a mammalian patient in need of such treatment, comprising administering to said patient a compound in accordance with formula I as described above in an amount effective to treat atherosclerosis.

Another aspect of the invention that is of interest relates to a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I as described above in an amount that is effective to treat said condition.

Another aspect of the invention that is of interest relates to a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound in accordance with formula I as described above in an amount that is effective to delay the onset of said condition.

Another aspect of the invention that is of interest relates to a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I as described above in an amount that is effective to reduce the risk of developing said condition.

Another aspect of the invention that is of interest relates to a method of treating a condition selected from the group consisting of:

(1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (1.3) vascular restenosis, (14) pancreatitis, (15) abdominal obesity, (16) neurodegenerative disease, (17)retinopathy, (18) nephropathy, (19) neuropathy, (20) Syndrome X, and other conditions and disorders where insulin resistance is a component, in a mammalian patient in need of such treatment, comprising administering to the patient effective amounts of a compound of formula I as described above, and a compound selected from the group consisting of:

(a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics, and GLP-1 receptor agonists; (h) GIP,GIP mimetics, and GIP receptor agonists; (i) PACAP, PACAP mimetics, and PACAP receptor 3 agonists; 0) cholesterol lowering agents selected from the group consisting of (i) HNG-CoA reductase inhibitors, (ii) sequestrants, (iii) nicotinyl alcohol, nicotinic acid and salts thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (1) antiobesity compounds; (m) an ileal bile acid transporter inhibitor; (n) anti-inflammatory agents excluding glucocorticoids; and (o) protein tyrosine phosphatase-1B (PTP-IB) inhibitors, said compounds being administered to the patient in amounts that are effective to treat said condition.

Another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I as described above and an HMG-CoA reductase inhibitor wherein the HMG-CoA reductase inhibitor is a statin.

Even more particularly, another aspect of the invention that is of interest relates to a method of treating a condition selected from the group consisting of hypercholesterolemia, atherosclerosis, low HDL levels, high LDL levels, hyperlipidemia, hypertriglyceridernia and dyslipidemia, in a mammalian patient in need of such treatment, comprising administering to the patient therapeutically effective amounts of a compound of formula I as described above and an HMG-CoA reductase inhibitor, wherein the HMG CoA reductase inhibitor is a statin selected from the group consisting of lovastatin, simvastatin, pravastatin, fluvastatin, atorvastatin, itavastatin, ZD-4522 and rivastatin.

Another aspect of the invention that is of interest relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment therapeutically effective amounts of a compound of formula I as described above and an HMG-CoA reductase inhibitor.

Another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor.

More particularly, another aspect of the invention that is of interest relates to a method for delaying the onset of, or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin.

Even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is a statin selected from the group consisting of: lovastatin, simvastatin, pravastatin, fluvastatin, atorvastatin, itavastatin, ZD-4522 and rivastatin.

Yet even more particularly, another aspect of the invention that is of interest relates to a method for delaying the onset or reducing the risk of developing atherosclerosis in a human patient in need of such treatment comprising administering to said patient effective amounts of a compound of formula I as described above and an HMG-CoA reductase inhibitor wherein the HMG-CoA reductase inhibitor is simvastatin.

Another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor. More particularly, another aspect of the invention that is of interest relates to a method for delaying the onset or reducing the risk of developing atherosclerosis in a human patient in need of such treatment comprising administering to said patient effective amounts of a compound of formula I as described above and a cholesterol absorption inhibitor wherein the cholesterol absorption inhibitor is ezetimibe.

Another aspect of the invention that is of interest relates to a method for delaying the onset or reducing the risk of developing the other diseases and conditions mentioned above, in a mammalian patient in need of such treatment comprising administering.to said patient effective amounts of a compound of formula I as described above, and a cholesterol absorption inhibitor.

More particularly, another aspect of the invention that is of interest relates to a method for delaying the onset or reducing the risk of developing the other diseases and conditions mentioned above, in a human patient in need of such treatment comprising administering to said patient effective amounts of a compound of formula I as described above, and a cholesterol absorption inhibitor, wherein the cholesterol absorption inhibitor is ezetimibe.

Another aspect of the invention that is of interest relates to a pharmaceutical composition comprising (1) a compound of formula I as described above; (2) a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) other glucagon receptor antagonists; (g) GLP-1, GLP-1 mimetics and GLP-1 receptor agonists; (h) GIP, GIP mimetics and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B(PTP-1B) inhibitors; and (3) a pharmaceutically acceptable carrier.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds of Formula I.

Salts and Solvates

Salts and solvates of compounds of formula I are included in the present invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I are intended to include the pharmaceutically acceptable salts and solvates.

This invention relates to a method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals associated with elevated levels of glucose, comprised of combining the compound of formula I with the carrier materials to provide the medicament.

Dose Ranges

The prophylactic or therapeutic dose of a compound of formula I will, of course, vary with the nature or severity of the condition to be treated, the particular compound selected and its route of administration. It will also vary according to the age, weight and response of the individual patient. In general, the daily dose range lies within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds of formula I, as well as the pharmaceutically acceptable salts and solvates thereof, for adults range from about 0.1 mg to about 1.0 g per day, preferably about 1 mg to about 500 mg, in single or divided doses. Representative dosages of compounds used in combination with the compounds of formula I are known, or the determination thereof is within the level of skill in the art, taking into account the description provided herein.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet contains from about 1 mg to about 1.0 g of the active ingredient and each cachet or capsule contains from about 1 to about 500 mg of the active ingredient.

The following are examples of pharmaceutical dosage forms containing a compound of Formula I:

| Injectable Suspension (im.) | mg/mL | Tablet | Mg/tablet |
|---|---|---|---|
| Compound of Formula 1 | 10.0 | Compound of Formula 1 | 25.0 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 4.35 |
| Benzalkonium chloride | 1.0 | Magnesium Stearate | 2.5 |
| Water for injection | t.d. 1.0 mL | Total | 500 mg |

| Capsule | mg/capsule | Aerosol | Per Canister |
|---|---|---|---|
| Compound of Formula 1 | 25.0 | Compound of Formula 1 | 250 mg |
| Lactose | 735 | Lecithin, NF Liq. Conc. | 1.2 mg |
| Mg Stearate | 1.5 | Trichloromethane, NF | 4.025 g |
| Total | 600 mg | Dichlorodifluoromethane, NF | 12.15 g |

Combination Therapy

As previously described, the compounds of Formula I may be used in combination with other drugs that are used in the treatment/prevention/delaying the onset of type 2 diabetes mellitus, as well as other diseases and conditions described herein, for which compounds of Formula I are useful. Other drugs may be administered, by a route and in an amount commonly used, contemporaneously or sequentially with a compound of Formula I. When a compound of Formula I is used contemporaneously with one or more other drugs, a combination pharmaceutical composition containing such other drugs in addition to the compound of Formula I is preferred. Accordingly, the pharmaceutical compositions of the present invention include those that alternatively contain one or more other active ingredients, in addition to a compound of Formula I. Examples of other active ingredients that may be combined with a compound of Formula I, either administered separately or in the same pharmaceutical compositions, include, but are not limited to: (a) biguanides (e g., buformin, metformin, phenformin), (b) PPAR agonists (e.g., troglitazone, pioglitazone, rosiglitazone), (c) insulin, (d) somatostatin, (e) alpha-glucosidase inhibitors (e.g., voglibose, miglitol, acarbose), (f) DP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each active ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: (1) a compound according to formula I, (2) a compound selected from the group consisting of: (a) DP-WV inhibitors; (b) insulin sensitizers selected from the group consisting of (i) PPAR agonists and (ii) biguanides; (c) insulin and insulin mimetics; (d) sulfonylureas and other insulin secretagogues; (e) a-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and (3) a pharmaceutically acceptable carrier.

The compounds of formula I can be synthesized in accordance with the general schemes provided below, taking into account the specific examples that are provided. Throughout the synthesis schemes, abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DIAD = diisopropyl-azodicarboxylate |
| DMAP = 4-Dimethylamino-pyridine | DMF = N,N-dimethylformamide |
| EtOAc = ethyl acetate | EtOH = ethanol |
| eq. = equivalent(s) | FAB-mass spectrum = Fast atom bombardment-mass spectroscopy |
| HOAc = acetic acid | |
| HOBT, HOBt = Hydroxybenztriazole | HPLC = High pressure liquid chromatography |
| Me = methyl | LAH = Lithium aluminum hydride |
| Ph = phenyl | PBS = phosphate buffer saline |
| THF = Tetrahydrofuran | TFA = Trifluoroacetic acid |
| $C_6H_{11}$ = cyclohexyl | $NMe_2$ = dimethylamino |
| iPr = isopropyl | 2ClPh = 2-chlorophenyl |
| 2,4-diClPh = 2,4-dichlorophenyl | Py, Pyr = pyridyl |

Compounds of the present invention may be prepared according to the methodology outlined in the following general synthetic schemes.

In one embodiment of the present invention, the compounds (I) may be prepared from intermediate III (vide infra),

III where $R^2$ is as defined above with respect to formula I and R represents an alkyl group. Compounds III, are known in the literature or may be conveniently prepared by a variety of methods familiar to those skilled in the art such as described in Katritsky et al., Advances in Heterocyclic Chemistry, Vol. 6, pg 347-429. One route is illustrated in Scheme 1. A diester of oxalic acid 1, which may be commercially available or readily prepared from the corresponding carboxylic acid by esterification using, for example, methanol or ethanol containing an acid such as sulphuric acid, is condensed with the anion of methyl ketone 2 to give diketoester 3, *J. Heterocyclic Chem,* 26, 1389 (1989). The reaction is carried out using a base such as lithium hexamethyldisilazide in a polar aprotic solvent such as tetrahydrofuran (THF) at −78° C. to 0° C. for 2 to 24 h, see March, Advanced Organic Chemistry, 3$^{rd}$ Ed., pg 439 and ref. therein. Compounds such as 2 are commercially available or can be prepared by a variety of methods familiar to those skilled in the art. Diketone 3 is then condensed with hydrazine in a polar solvent such as ethanol which may contain an acid such as acetic or hydrochloric acid, for 16 to 24 h at a temperature of 0 to 25° C.

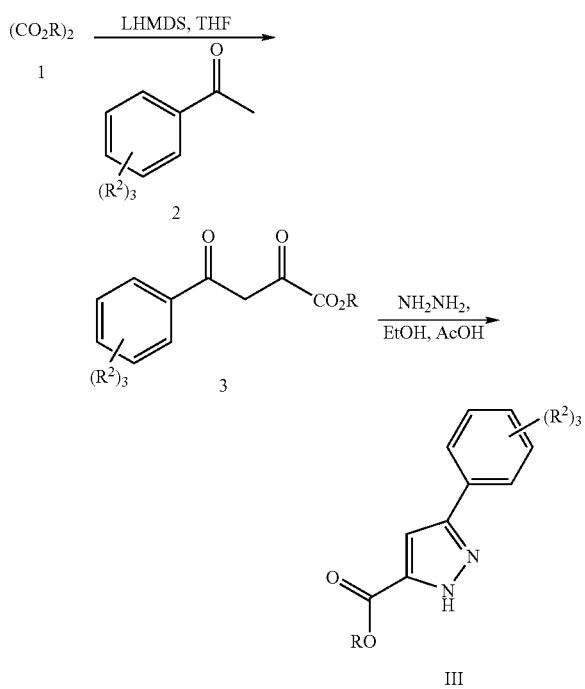

SCHEME 1

An alternate route to intermediate mi involves condensation of alkynyl ketone 4 with hydrazine as shown in Scheme 2 and described in Cabarrocas et. al., Tetrahedron Asymmetry, Vol. 11, pg 2483-2493, 2000 and references therein. This is generally carried out in a polar solvent such as DMF at temperatures of from about 0 to 25° C. for about 16 to 24 h. Preparation of the intermediate 4 involves coupling of the commercially available alkyne 5 with the Weinreb amide of an appropriately functionalised carboxylic acid using a hindered base such as lithium diisopropylamide or butyl lithium in a polar aprotic solvent such as THF at about −78° C. This reaction is described in detail in Tetrahedron Lett., Vol. 22, pg 3815, 1981.

SCHEME 2

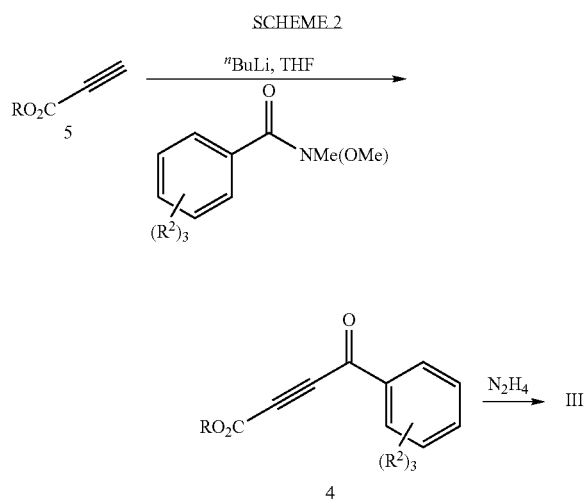

Intermediate III can then be converted to compounds of formula Ia and Ib as shown below in Scheme 3. Alkylation of pyrazole III with, for example, 4-carbomethoxy benzylbromide can be achieved following deprotonation of the pyrazole with a base such as sodium hydride or cesium carbonate in a polar solvent, generally dimethyl formamide (DMF), at about 0 to 25° C. for about 3 to 24 h. Alternatively, pyrazole III can be alkylated using Mitsonobu conditions with a benzylic alcohol 6 which is prepared from reduction of a carbonyl derivative. In most cases the alkylation gives predominantly compound 7, however in some cases mixtures of isomers will be formed. These are generally separable by recrystallization, trituration, preparative thin layer chromatography, or flash chromatography on silica gel as described by W. C. Still et al, *J. Org. Chem.*, 43, 2923, (1978), or HPLC. Compounds purified by HPLC may be isolated as the corresponding salt. When X is a nitrogen atom, a pyridylmethylbromide alkylating agent 8 should be utilized. These can be readily prepared from commercially available starting materials for example from 6-methylnicotinate by radical bromination. This reaction can be carried out using a brominating agent such as N-bromosuccinimide and a radical initiator normally azobisisobutyronitrile (AIBN) in an inert solvent such as tetrachloromethane (see Pizey, Ref. 82, vol 2, p1-63, 1974).

Release of the pyrazole carboxylic acid 9 can be achieved selectively in the presence of the benzyl ester if the former is orthogonally protected ie R=$^t$Bu. This is achieved most conveniently by treatment with trifluoroacetic acid in methylene chloride for 0.5-3h at ambient temperature. Coupling of the acid with an aliphatic or aromatic amine 10 is carried out with standard peptide coupling conditions, for example using 1-ethyl-3-(3-dimethylaminopropyl)-carbodiimide (EDC), 1-hydroxy-7-azabenzotriazole (HOAt), and a base, generally diisopropylethylamine, in a solvent such as N,N-dimethylformamide (DMF) or methylene chloride for 3 to 48 hours at ambient temperature to yield amide 11. Saponification of the methyl ester of 11 is then achieved using a base such as aqueous lithium or sodium hydroxide in a polar solvent such as tetrahydrofuran, methanol, ethanol or a mixture of similar solvents. Coupling of the acid with an amine, generally 5-aminotetrazole 12 or a beta alanine derivative 13 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ia and, following deprotection, Ib.

The product is purified from unwanted side products by recrystallization, trituration, preparative thin layer chromatography, flash chromatography on silica gel as described by W. C. Still et al, *J. Org. Chem.*, 43, 2923, (1978), or BPLC. Purification of intermediates is achieved in the same manner. As will be understood by those skilled in the art, for the preparation of enantiomerically pure compounds, enantiomerically pure starting materials should be used.

In some cases, the product from the reactions described in Scheme 3 will be further modified. These manipulations may include, but are not limited to substitution, reduction, oxidation, alkylation, acylation, and hydrolysis reactions, which are commonly known to those skilled in the art. One such modification is saponification of a methyl or removal of a tert butyl ester, as shown, this is achieved using a base such as aqueous lithium or sodium hydroxide in a polar solvent such as tetrahydrofuran, methanol, ethanol or a mixture of similar solvents or by treatment with trifluoroacetic acid in methylene chloride at ambient temperatures for 0.5-3 h.

SCHEME 3

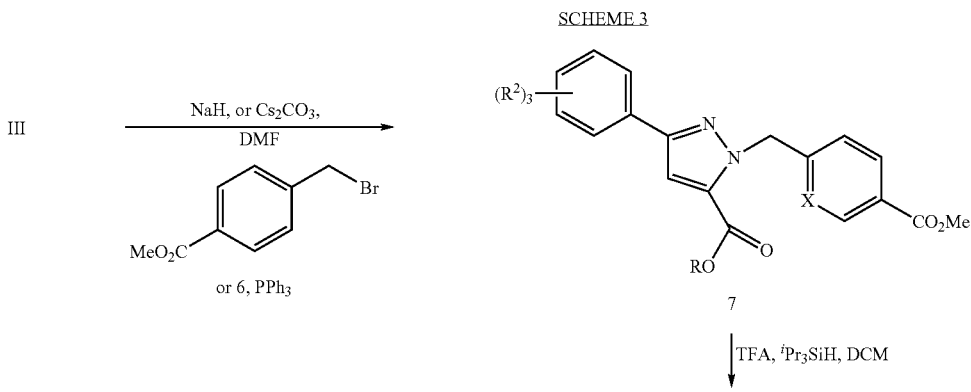

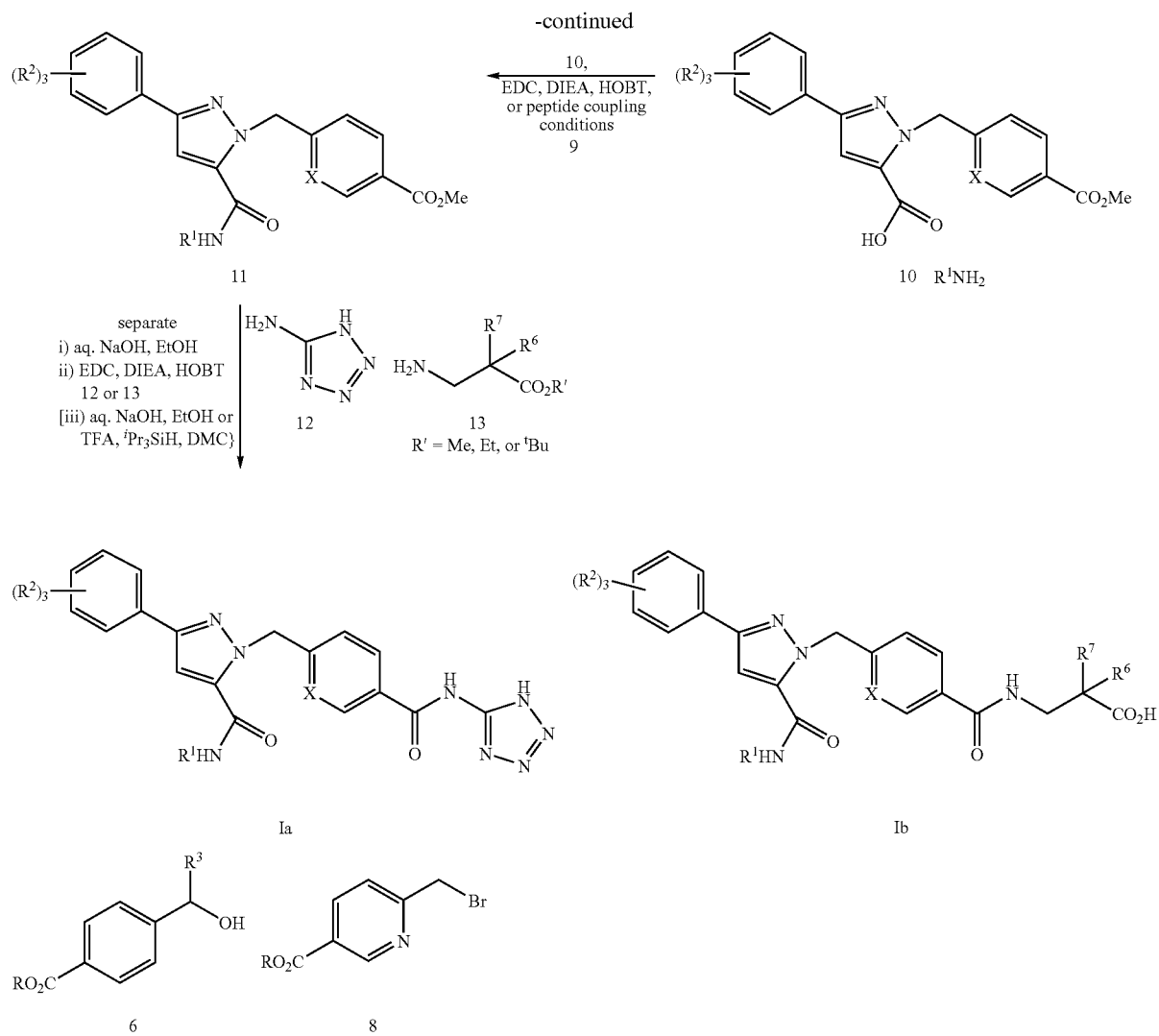

In another embodiment of the present invention, the compounds Ic and Id where B represents —C(O)NHR may be prepared as described in Scheme 4 from the condensation of diketo ester 3 with benzylhydrazine 14 (vide infra ) to give intermediate 17. Benzyl hydrazine 14 may be prepared from the corresponding carbonyl analog by condensation with tert-butylcarbazate in the presence of acetic acid in a nonpolar solvent such as toluene at elevated temperatures for 16 to 24 h. The intermediate 15 is then reduced with a hydride reducing agent such as sodium cyanoborohydride and 1 equivalent of p-toluenesulfonic acid, which should be added in a dropwise fashion. Alternatively, acetic acid can be used as a co-solvent for the reaction in which case toluenesulfonic acid is not used. The reaction is carried out in a polar aprotic solvent such as tetrahydrofuran (THF) for 16-48 h at ambient temperature. Following aqueous work-up, the borane complex can be decomposed by slowly adding an aqueous solution of sodium hydroxide or other strong base to give carbamate 16 (see Calabretta et al., *Synthesis,* 1991, 536). Deprotection of the BOC group was effected by treatment with an acid such as trifluoroacetic acid in methylene chloride at ambient temperature for 0.25-2h. The reaction can be performed with or without the addition of triisopropylsilane. The hydrazine 14 can either be used as its trifluoroacetate salt directly from the deprotection, or the free-base can be prepared and the material isolated as the hydrochloride salt by addition of aqueous hydrochloric acid and evaporation of the solvent. In the case ($R^3$ not H) that intermediate 16 contains a chiral center, the enantiomers can be resolved at this point by chromatography using a homochiral stationary phase. Alternatively, hydrazone 15 can be directly reduced with hydrogen and a chiral catalyst such as a rhodium DuPHOS complex as described in Burk et al., *Tetrahedron,* 1994, 50, 4399. The solvent used for the reaction was generally an alcohol such as 2-propanol and elevated hydrogen pressure was used. This reaction would give material of enriched enantioselectivity which could be further purified by chiral chromatography as described above. The intermediate 17 is carried through to final products Ic and Id using chemistry analogous to that described above for conversion of 7 to Ia and Ib in Scheme 3, vide supra.

SCHEME 4

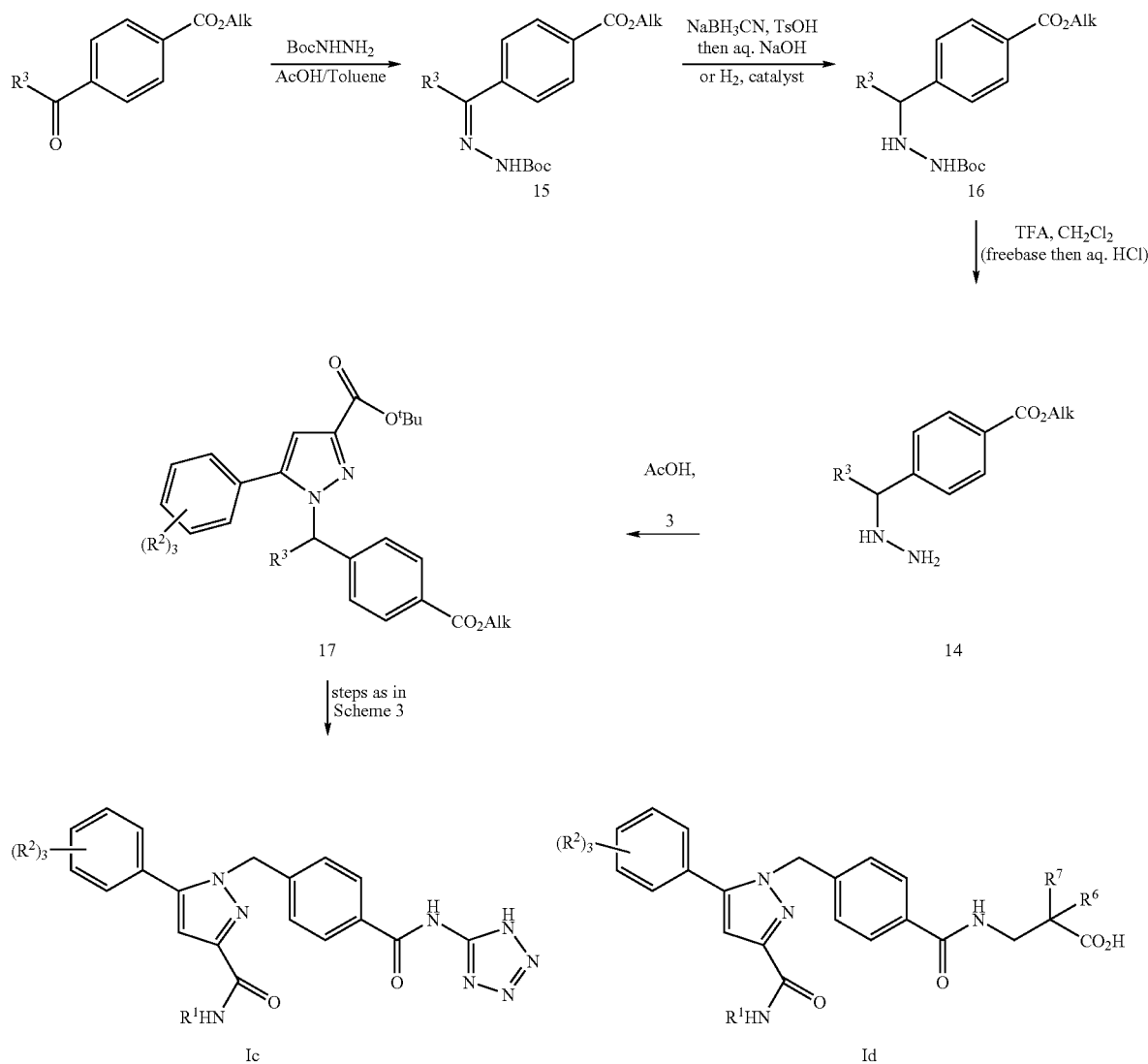

In another embodiment of the present invention, where Y is oxygen, the compounds (Ie) may be prepared as described in Scheme 5 from intermediate III, vide supra. Release of the pyrazole carboxylic acid can be achieved most conveniently by treatment with trifluoroacetic acid in methylene chloride for 0.5-3 h at ambient temperature. Coupling of the acid with an aliphatic or aromatic amine is carried out with standard peptide coupling conditions, for example using 1-ethyl-3-(3-dimethylaminopropyl)-carbodiimide (EDC), 1-hydroxy-7-azabenzotriazole (HOAt), and a base, generally diisopropylethylamine, in a solvent such as N,N-dimethylformamide (DMF) or methylene chloride for 3 to 48 hours at ambient temperature to yield amide 18. This can then be alkylated with an alkyl halide such as benzyl iodide 19 in a solvent such as DMF containing a base such as cesium carbonate or sodium hydride at 0-25° C. for 1-24 h. Release of the carboxylic acid is then achieved by saponification of a methyl or removal of a tert butyl ester, as shown, this is achieved using a base such as aqueous lithium or sodium hydroxide in a polar solvent such as tetrahydrofuran, methanol, ethanol or a mixture of similar solvents or by treatment with trifluoroacetic acid in methylene chloride at ambient temperatures for 0.5-3 h. Benzyl halides such as 19 are commercially available or can be prepared by anyone skilled in the art. For example, alkylation of the hydroxyl group of 4-hydroxy benzaldehyde with a reagent such as ethyl bromobutanoate is readily carried out with a base such as sodium hydride in a polar aprotic solvent such as DMF. The aldehyde can then be reduced with a hydride reducing agent such as sodium borohydride in an alcoholic solvent such as ethanol, followed by treatment with iodine and a triarylphosphine such as triphenylphosphine in a solvent, normally acetonitrile containing a base such as imidazole to give the compound 19. In this particular case release of the ester as described above reveals the final product Ie. In some cases, the product from the reactions described above will be further modified. These manipulations may include, but are not limited to substitution, reduction, oxidation, alkylation, acylation, and hydrolysis reactions, which are commonly known to those skilled in the art.

SCHEME 5

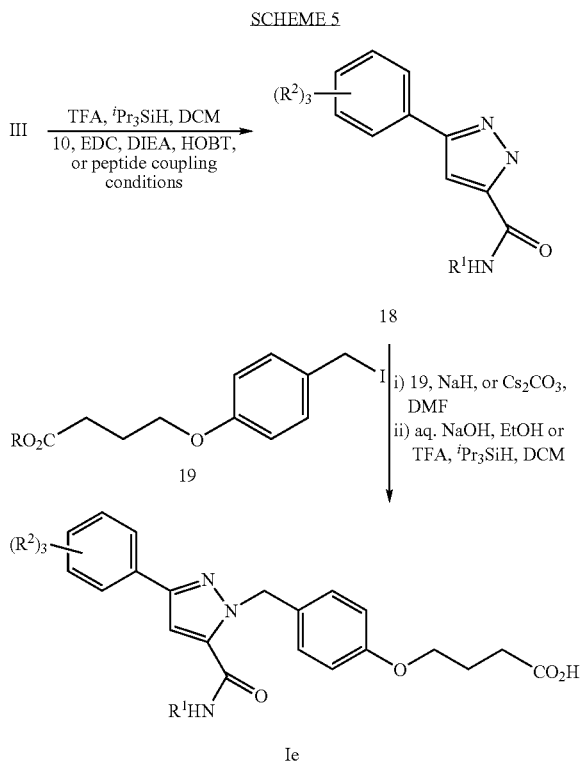

General experimental: Preparative HPLC was performed on an YMC-Pack Pro C18 column (150×20 mm i.d.) eluting at 20 mL/min with 0-100% acetonitrile in water (0.5% TFA).

The following examples are provided so that the invention might be more fully understood. They should not be construed as limiting the invention in any way.

EXAMPLE 1

N-(TRANS-4-TERT-BUTYLCYCLOHEXYL)-1-{4-[(1H-TETRAZOL-5-YLAMINO)CARBONYL]BENZYL}-3-(3,4,5-TRIFLUOROPBENYL)-1H-PYRAZOLE-5-CARBOXAMIDE

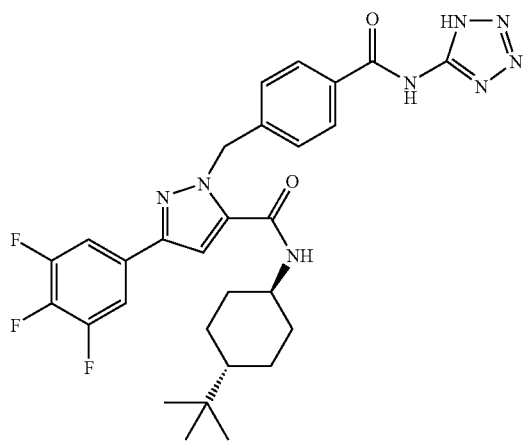

Step A. tert-Butyl 2,4-dioxo-4-(3,4,5-trifluorophenyl)butanoate

To a solution of 3',4',5'-trifluoro acetophenone (3.0 g, 17.22 mmol) in anhydrous ether (100 mL) cooled to −78° C. was added LHMDS (19 mL, 18.95 mmol). After 45 minutes at −78° C. di-tert-butyl oxalate (4.18 g, 20.66 mmol) was added as a solid. The reaction was warmed to room temperature and left stirring for 18 hours. The reaction was quenched by adding 1N HCl (150 mL). The resulting mixture was stirred for 45 minutes. The mixture was extracted with ethyl acetate washed with brine and dried over anhydrous $Na_2SO_4$. The solution was filtered and concentrated in vacuo to give a dark yellow solid. This material was used in the next step without any further purification. LC-MS: 2.67 min; (M+H−56)=230.0

Step B. tert-Butyl 3-(3,4,5-trifluorophenyl)-1H-pyrazole-5-carboxulate

To a solution of the intermediate from step A (5.7 g, 17.2 mmol) in ethanol (90 mL) was added hydrazine (35% by wt. solution, 1.71 mL, 18.95 mmol) followed by AcOH (10 mL) and the resulting mixture was stirred at room temperature. After 2 hours, the reaction mixture was concentrated in vacuo. The residue was dissolved in ethyl acetate and washed with saturated $NaHCO_3$ solution, dried over anhydrous $Na_2SO_4$, filtered and concentrated in vacuo. This material was used in the next step without any further purification. An off white solid was obtained. $^1$H NMR ($CD_3OD$, 500 MHz): 7.59 (bt, 2H), 7.13 (s, 1H), 1.65 (s, 9H). LC-MS: 3.64 min; (M+H−56)=243.1.

Step C. tert-Butyl 1-[4-(methoxycarbonyl)benzyl]-3-(3,4,5-trifluorophenyl)-1H-pyrazole-5-carboxylate To a solution of the intermediate from step B (1.0 g, 3.35 mmol) in DMF (20 mL) was added methyl 4-(bromo-methyl)benzoate (0.84 g, 3.68 mmol) and cesium carbonate (1.63 g, 5.02 mmol). After stirring the reaction at room temperature for 18 hours, it was concentrated in vacuo. The residue was suspended in water and extracted with ethyl acetate (3×). The organic layer was washed with saturated NaCl solution and dried over anhydrous $Na_2SO_4$. The solution was filtered and concentrated in vacuo. The residue was purified on Biotage flash 40 M cartridge using 15% ethyl acetate-hexanes. A white solid obtained. $^1$H NMR ($CDCl_3$, 500 MHz): 8.03 (d, J=10.0 Hz, 2H), 7.48 (dd, J=6.6, 8.2 Hz, 2H), 7.34 (d, J=8.2 Hz, 2H), 7.06 (s, 1H), 5.58 (s, 2H), 3.93 (s, 3H), 1.57 (s, 9H). LC-MS: 4.4 min; (M+H)=447.15.

Step D. 1-[4-(methoxycarbonyl)benzyl]-3-(3,4,5-trifluorophenyl)-1H-pyrazole-5-carboxylic acid To a solution of the intermediate from step C (1.3 g, 3 mmol) in dichloromethane (10 mL) was added TFA (10 mL). After stirring the reaction at room temperature for 18 hours, it was concentrated in vacuo, azeotroped with toluene (3×) and used in the next step without any further purification. $^1$H NMR ($CD_3OD$, 500 MHz): 7.97 (d, J=8.2 Hz, 2H), 7.63 (dd, J=6.9, 9.0 Hz, 2H), 7.33 (s, 1H), 7.31 (d, J=8.3 Hz, 2H), 5.58 (s, 2H), 3.88 (s, 3H). LC-MS: 3.68 min; (M+H)=391.1.

Step E. Methyl 4-{[5-{[(trans-4-tert-butylcyclohexyl)amino]carbonyl}-3-(3,4,5-trifluorophenyl)-1H-pyrazol-1-yl]methyl}benzoate To a solution of the intermediate from step D (0.39 g, 1.0 mmol) in DMF (2 mL) was added 4-tert-butyl cyclohexylamine (268 μL, 1.5 mmol), HOAt (0.2 g, 1.5 mmol), DIEA (0.52 mL, 3.0 mmol) and EDC (0.29 g, 1.5 mmol). The resulting solution was stirred at room temperature for 48 hours. The reaction was diluted with ethyl acetate and washed with 1N HCl, saturated NaHCO$_3$, and saturated NaCl. The organic layer was dried over anhydrous Na$_2$SO$_4$, filtered and concentrated in vacuo. The residue was purified on Biotage Quad 3 system using 30% ethyl acetate-hexanes. The trans and cis isomers were obtained in a 3:1 ratio. Isomer A (trans isomer): $^1$H NMR (CDCl$_3$, 500 MHz): 8.02 (d, J=8.4 Hz, 2H), 7.46 (dd, J=6.7, 7.9 Hz, 2H), 7.41 (d, J=8.2Hz, 2H), 6.75 (s, 1H), 5.86 (s, 2H), 5.83 (d, J=8.2 Hz, 1H), 3.93 (s, 3H), 3.8 (m, 1H), 2.11 (bm, 2H), 1.18 (bm, 2H), 1.2-1.0 (m, 3H), 0.91 (s, 9H). LC-MS: 3.07 min; (M+H)=528.2. Isomer B (cis isomer): $^1$H NMR (CDCl$_3$, 500 MHz): 8.01 (d, J=8.0 Hz, 2H), 7.48 (t, J=6.6 Hz, 2H), 7.39 (d, J=8.0 Hz, 2H), 6.73 (s, 1H), 6.08 (d, J=7.1 Hz, 1H), 5.84 (s, 2H), 4.23 (m, 1H), 3.92 (s, 3H), 1.94 (d, J=14.2 Hz, 2H), 1.71 (d, J=11.2 Hz, 2H), 1.61 (m, 2H), 1.1 (m, 2H), 0.89 (s, 9H). LC-MS: 3.07 min; (M+H)= 528.2.

Step F. 4-{[5-{[(trans-4-tert-butylcyclohexyl)amino]carbonyl}-3-(3,4,5-trifluorophenyl)-1H-pyrazol-1-yl]methyl}benzoic acid To a solution of the intermediate from step E (isomer A, 0.3 g, 0.56 mmol) in 10 ml of THF/MeOH was added 5 N NaOH (1 mL). The reaction was stirred at room temperature for 2 hours and concentrated in vacuo. The residue was acidified with 1N HCl (10 ml). The resulting mixture was extracted with ethyl acetate, dried over anhydrous Na$_2$SO$_4$ filtered and concentrated in vacuo. This material was used in the next step without any further purification. $^1$H NMR (CD$_3$OD, 500 MHz): 8.26 (d, J=2.1 Hz, 1H), 7.96 (d, J=8.3 Hz, 1H), 7.59 (dd, J=6.6, 8.9 Hz, 1H), 7.31 (d, J=8.3 Hz, 1H), 7.17 (s, 1H), 5.83 (s, 2H), 3.7 (m, 1H), 1.95 (d, J=10.1 Hz, 1H), 1.86 (d, J=10.3 Hz, 1H), 1.3 (m, 2H), 1.15 (m, 2H), 1.0 (m, 1H), 0.88 (s, 9H). LC-MS: 4.25 min; (M+H)=514.2.

Step G. N-(trans-4-tert-butylcyclohexyl)-1-{4-[(1H-tetrazol-5-ylamino)carbonyl]benzyl}-3-(3,4,5-trifluorophenyl)-1H-pyrazole-5-carboxamide To a solution of the intermediate from step F (90 mg, 0.175 mmol) in DMF was added HOAt (36 mg, 0.26 mmol), DIEA (92 μL, 0.52 mmol), amino tetrazole (45 mg, 0.52 mmol) and EDC (50 mg, 0.26 mmol). The reaction was left stirring at room temperature for 18 hours. The reaction mixture was diluted with ethyl acetate (20 mL) and washed with 1N HCl. The organic layer was dried over anhydrous Na$_2$SO$_4$, filtered and concentrated in vacuo. The residue was purified on the Gilson reverse phase HPLC to give the title compound. $^1$H NMR (DMSO, 500 MHz): 8.42 (d, J=8.0 Hz, 1H), 8.03 (d, J=8.2 Hz, 2H), 7.68 (dd, J=6.6, 8.7 Hz, 2H), 7.39 (s, 1H), 7.35 (d, J=8.3 Hz, 2H), 5.81 (s, 2H), 3.63 (m, 1H), 1.87 (d, J=10.9 Hz, 2H), 1.76 (d, J=11.7 Hz, 2H), 1.2-1.0 (m, 4H), 0.83 (s, 9H). LC-MS: 2.50 min; (M+H)=581.3.

EXAMPLE 2

N-(4-{[5-{[(TRANS-4-TERT-BUTYLCYCLOHEXYL)AMINO]CARBONYL}-3-(3,4,5-TRIFLUOROPHENYL)-1H-PYRAZOL-1-YL]METHYL}BENZOYL)-β-ALANINE

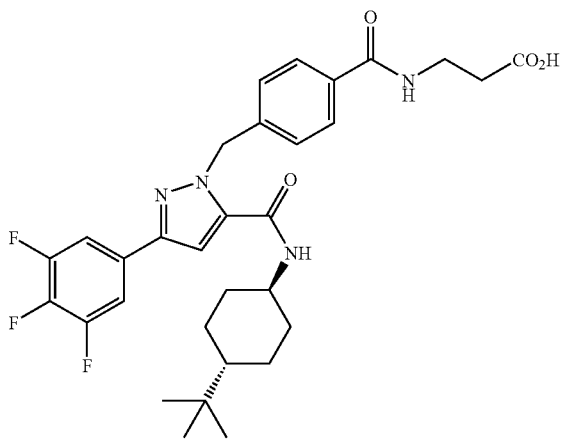

Step A. tert-Butyl N-(4-{[5-{[(trans-4-tert-butylcyclohexyl)amino]carbonyl}-3-(3,4,5-trifluorophenyl)-1H-pyrazol-1-yl]methyl}benzoyl)-β-alaninate To a solution of the intermediate from example 1 step F (90 mg, 0.175 mmol) in DMF was added HOAt (36 mg, 0.26 mmol), DIEA (92 μL, 0.52 mmol), β-alanine-tert-butyl ester (48 mg, 0.26 mmol) and EDC (50 mg, 0.26 mmol). After stirring the reaction at room temperature for 18 hours it was diluted with ethyl acetate (20 mL), washed with 1N HCl, saturated NaHCO$_3$, and saturated NaCl. The organic layer was dried over anhydrous Na$_2$SO$_4$, filtered and concentrated in vacuo. The residue was purified on the Biotage quad 3 using 30% ethyl acetate-hexanes to give the title compound. $^1$H NMR (CDCl$_3$, 500 MHz): 7.72 (d, J=8.3 Hz, 2H), 7.45 (t, J=6.9 Hz, 2H), 7.40 (d, J=8.2 Hz, 2H), 6.87 (bt, J=5.5 Hz, 1H), 6.73 (s, 1H), 5.83 (s, 2H), 3.9 (m, 1H), 3.7 (q, J=6.0 Hz, 2H), 2.57 (t, J=6.0 Hz, 2H), 2.1 (bm, 2H), 1.9 (bm, 2H), 1.47 (s, 9H), 1.2-1.4 (m, 4H), 0.88 (s, 9H). LC-MS: 4.55 min; (M+H)=641.5.

Step B. N-(4-{[5-{[(trans-4-tert-butylcyclohexyl)amino]carbonyl}-3-(3,4,5-trifluorophenyl)-1H-pyrazol-1-yl]methyl}benzoyl)-β-alanine To a solution of the intermediate from step, A in DCM (2 mL) was added TFA (2 mL). The resulting solution was stirred at room temperature for 1 hour. The reaction mixture was concentrated in vacuo and azeotroped with toluene to give the title compound. $^1$H NMR (DMSO, 500 MHz): 8.47 (t, J=5.2 Hz, 1H), 8.39 (d, J=8.0 Hz, 1H), 7.75 (d, J=8.0 Hz, 2H), 7.66 (t, J=8.2 Hz, 2H), 7.35 (s, 1H), 7.26 (d, J=8.0 Hz, 2H), 5.75 (s, 2H), 3.63 (m, 1H), 3.42 (q, J=6.7 Hz, 2H), 1.87 (d, J=10.3 Hz, 2H), 1.76 (d, J=12.1 Hz, 2H), 1.27 (q, J=11.6 Hz, 2H), 1.08 (q, J=10.9 Hz, 2H), 0.83 (s, (H). LC-MS: 2.68 min; (M+H)=585.3.

EXAMPLE 3

N-(CIS-4-TERT-BUTYLCYCLOHEXYL)-1-{4-[(1H-TETRAZOL-5-YLAMINO)CARBONYL]BENZYL}-3-(3,4,5-TRIFLUOROPHENYL)-1H-PYRAZOLE-5-CARBOXAMIDE

EXAMPLE 4

N-(4-{[5-{[(CIS-4-TERT-BUTYLCYCLOHEXYL)AMINO]CARBONYL}-3-(3,4,5-TRIFLUOROPHENYL)-1H-PYRAZOL-1-YL]METHYL}BENZOYL)-β-ALANINE

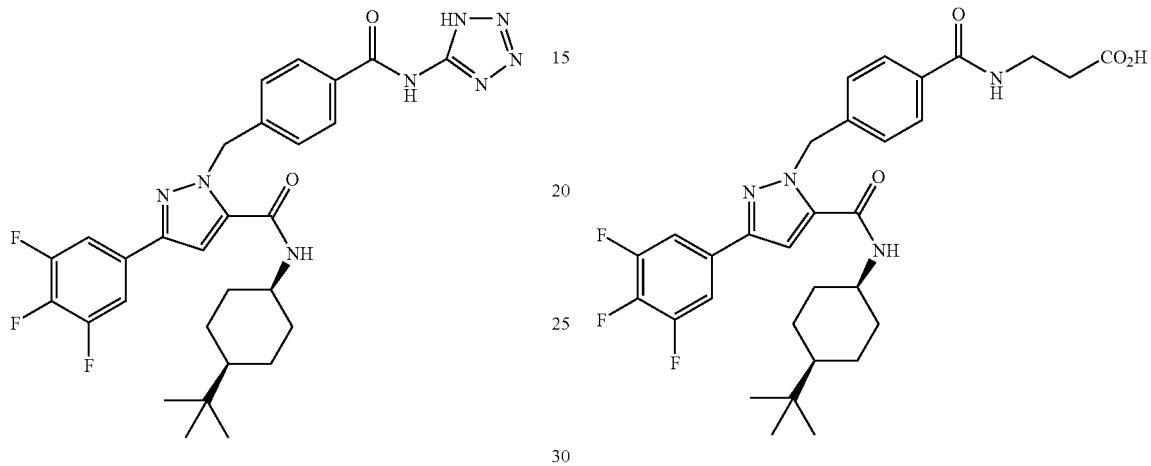

Step A. 4-{[5-{[(cis-4-tert-butylcyclohexyl)amino]carbonyl}-3-(3,4,5-trifluorophenyl)-1H-pyrazol-1-yl]methyl}benzoic acid To a solution of the intermediate from example 1 step E (isomer B, 0.11 g, 0.21 mmol) in 10 ml of THF/MeOH was added 5 N NaOH (1 mL). After stirring the reaction at room temperature for 2 hours, it was concentrated in vacuo. The residue was acidified with 1N HCl (10 ml). The resulting mixture was extracted with ethyl acetate, dried over anhydrous $Na_2SO_4$ filtered and concentrated in vacuo. This material was used in the next step without any further purification. LC-MS: 4.25 min; (M+H)=514.2.

Step B N-(cis-4-tert-butylcyclohexyl)-1-{4-[(1H-tetrazol-5-ylamino)carbonyl]benzyl}-3-(3,4,5-trifluorophenyl)-1H-pyrazole-5-carboxamide To a solution of the intermediate from step A (45 mg, 0.09 mmol) in DMF was added HOAt (18 mg, 0.13 mmol), DIEA (46 μL, 0.26 mmol), amino tetrazole (23 mg, 0.26 mmol) and EDC (25 mg, 0.13 mmol). After stirring at room temperature for 18 hours, the reaction mixture was diluted with ethyl acetate (20 mL) and washed with 1N HCl. The organic layer was dried over anhydrous $Na_2SO_4$, filtered and concentrated in vacuo. The residue was purified on the Gilson reverse phase HPLC to give the title compound. $^1$H NMR (DMSO, 500 MHz): 8.16 (d, J=6.7 Hz, 1H), 8.05 (d, J=8.2 Hz, 2H), 7.73 (dd, J=6.7, 6.3 Hz, 2H), 7.41 (s, 1H), 7.34 (d, J=8.5 Hz, 2H), 5.74 (s, 2H), 3.98 (bs, 1H), 1.8 (d, J=11.9 Hz, 2H), 1.5 (bm, 3H), 1.4 (m, 2H), 1.1 (m, 1H0, 0.78 (s, (H). LC-MS: 2.51 min; (M+H)=581.3.

Step A. tert-Butyl N-(4-{[5-{[(cis-4-tert-butylcyclohexyl)amino]carbonyl}-3-(3.45-trifluorophenyl)-1H-pyrazol-1-yl]methyl}benzoyl)-β-alaninate To a solution of the intermediate from example 3 step A (45 mg, 0.09 mmol) in DMF was added HOAt (18 mg, 0.13 mmol), DIEA (46 μL, 0.26 mmol), β-alanine-tert-butyl ester (24 mg, 0.13 mmol) and EDC (25 mg, 0.13 mmol). The resulting solution was left stirring at room temperature for 18 hours. The reaction mixture was diluted with ethyl acetate (20 mL) and washed with 1N HCl, saturated $NaHCO_3$, and saturated NaCl. The organic layer was dried over anhydrous $Na_2SO_4$, filtered and concentrated in vacuo. The residue was purified on the Biotage quad 3 using 30% ethyl acetate-hexanes to give the desired compound. LC-MS=4.55 min; (M+H)=641.3.

Step B. N-(4-{[5-{[(Cis-4-tert-butylcyclohexyl)amino]carbonyl}-3-(3,4,5-trifluorophenyl)-1H-pyrazol-1-yl]methyl}benzoyl)-β-alanine To a solution of the intermediate from step A in DCM (2 mL) was added TFA (2 mL). After stirring at room temperature for 1 hour, the reaction mixture was concentrated in vacuo and azeotroped with toluene (3x) to give the title compound. $^1$H NMR (DMSO, 500 MHz): 8.48 (t, J=5.5 Hz, 1H), 8.15 (d, J=6.6 Hz, 1H), 7.76 (d, J=8.3 Hz, 2H), 7.7 (dd, J=6.9, 8.9 Hz, 2H), 7.37 (s, 1H), 7.24 (d, J=8.3 Hz, 2H), 5.69 (s, 2H), 3.98 (m, 1H), 3.41 (q, J=6.9 Hz, 2H), 2.46 (q, J=7.1 Hz, 2H), 1.83 (d, J=11.1 Hz, 2H), 1.4 (m, 3H), 1.2 (m, 2H), 0.95 (m, 1H), 0.81 (s, 9H). LC-MS: 2.46 min; (M+H)=585.4.

EXAMPLE 5

1-{4-[(1H-TETRAZOL-5-YLAMINO)CARBONYL]BENZYL}-N-[4-(TRIFLUOROMETHOXY)PHENYL]-3-(3,4,5-TRIFLUOROPHENYL)-1H-PYRAZOLE-5-CARBOXAMIDE

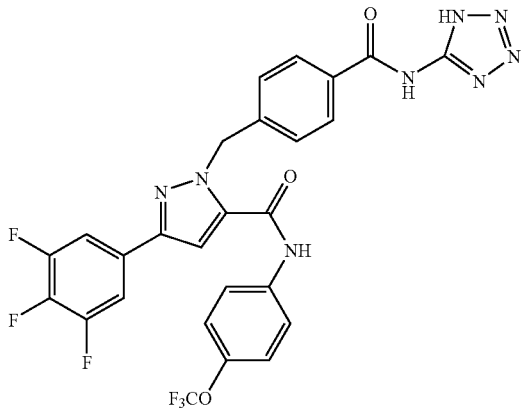

Step A. Methyl 4-{[5-({[4-(trifluoromethoxy)phenyl]amino}carbonyl)-3-(3,4,5-trifluorophenyl)-1H-pyrazol-1-yl]methyl}benzoate To a solution of the intermediate from example 1 step D (0.39 g, 1.0 mmol) in DMF (2 mL) was added 4-triflurometoxy aniline (83 µL, 0.615 mmol), HOAt (0.2 g, 1.5 mmol), DIEA (0.52 mL, 3.0 mmol) and EDC (0.29 g, 1.5 mmol). The resulting solution was stirred at room temperature for 48 hours. The reaction was diluted with ethyl acetate and washed with 1N HCl, saturated NaHCO$_3$, and saturated NaCl. The organic layer was dried over anhydrous Na$_2$SO$_4$, filtered and concentrated in vacuo. The residue was purified on Biotage Quad 3 system using 30% ethyl acetate-hexanes to give the title compound. $^1$H NMR (CDCl$_3$, 500 MHz): 8.03 (d, J=8.3 Hz, 2H), 7.72 (s, 1H), 7.64 (d, J=8.9 Hz, 2H), 7.49 (t, J=6.9 Hz, 2H), 7.43 (d, J=8.2 Hz, 2H), 7.29 (d, J=8.7 Hz, 2H), 6.96 (s, 1H), 5.91 (s, 2H), 3.93 (s, 3H). LC-MS: 4.32 min; (M+H)=550.1.

Step B. 4-{[5-({[4-(trifluoromethoxy)phenyl]amino}carbonyl)-3-(3,4,5-trifluorophenyl)-1H-pyrazol-1-yl]methyl}benzoic acid To a solution of the intermediate from step A (0.1 g, 0.18 mmol) in 10 ml of THF/MeOH was added 5 N NaOH (1 mL). After stirring the reaction at room temperature for 2 hours it was concentrated in vacuo. The residue was acidified with 1N HCl (10 ml) and was extracted with ethyl acetate, dried over anhydrous Na$_2$SO$_4$ filtered and concentrated in vacuo. This material was used in the next step without any further purification. $^1$H NMR (CD$_3$OD, 500 MHz): 7.96 (d, J=8.2 Hz, 2H), 7.73 (d, J=8.9 Hz, 2H), 7.62 (t, J=7.1 Hz, 2H), 7.4 (s, 1H), 7.35 (d, J=8.2 Hz, 2H), 7.27 (d, J=8.7 Hz, 2H), 5.88 (s, 2H). LC-MS=4.0 min; (M+H)=536.0.

Step C. 1-{4-[(1H-tetrazol-5-ylamino)carbonyl]benzyl}-N-[4-(trifluoromethoxy)phenyl]-3-(3,4,5-trifluorophenyl)-1H-pyrazole-5-carboxamide To a solution of the intermediate from step B (45 mg, 0.84 mmol) in DMF was added HOAt (17 mg, 0.126 mmol), DIEA (44 µL, 0.252 mmol), amino tetrazole (22 mg, 0.252 mmol) and EDC (24 mg, 0.126 mmol). The resulting solution was left stirring at room temperature for 18 hours. The reaction mixture was diluted with ethyl acetate (20 mL), and washed with 1N HCl. The organic layer was dried over anhydrous Na$_2$SO$_4$, filtered and concentrated in vacuo. The residue was purified on the Gilson reverse phase HPLC to give the title compound. 1H NMR (DMSO, 500 MHz): 8.04 (d, J=8.3 Hz, 2H), 7.82 (d, J=9.2 Hz, 2H), 7.74 (dd, J=6.9, 8.7 Hz, 2H), 7.64 (s, 1H), 7.38 (d, J=7.9 Hz, 2H), 5.85 (s, 2H). LC-MS: 2.56 min; (M+H)=603.1.

EXAMPLE 6

N-(4-{[5-({[4-(TRIFLUOROMETHOXY)PHENYL]AMINO}CARBONYL)-3-(3,4,5-TRIFLUOROPHENYL)-1H-PYRAZOL-1-YL]METHYL}BENZOYL)-β-ALANINE

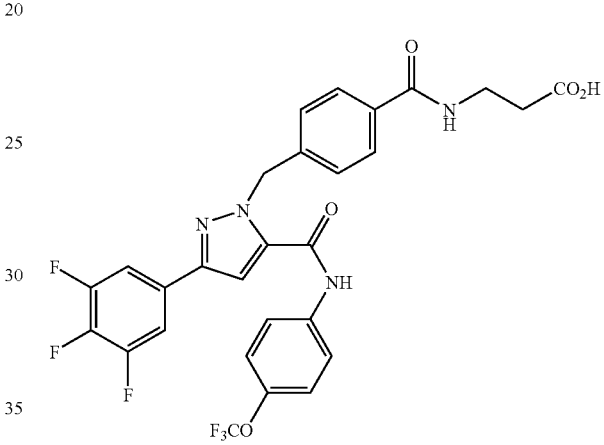

Step A. tert-Butyl N-(4-{[5-{[4-(trifluoromethoxy)phenyl]amino}carbonyl)-3-(3,4,5-trifluorophenyl)-1H-pyrazol-1-yl]methyl}benzoyl)-β-alaninate To a solution of the intermediate from example 5 step B (45 mg, 0.84 mmol) in DMF was added HOAt (17 mg, 0.126 mmol), DIEA (44 µL, 0.252 mmol), β-alanine-tert-butyl ester (22 mg, 0.252 mmol) and EDC (24 mg, 0.126 mmol). After stirring the reaction at room temperature for 18 hours, it was diluted with ethyl acetate (20 mL) and washed with 1N HCl, saturated NaHCO$_3$ and saturated NaCl solution. The organic layer was dried over anhydrous Na$_2$SO$_4$, filtered and concentrated in vacuo. The residue was purified on the Biotage quad 3 using 30% ethyl acetate-hexanes. LC-MS: 2.4 min; (M+H)= 663.2

Step B. N-(4-{[5-{[4-(trifluoromethoxy)phenyl]amino}carbonyl)-3-(3 4,5-trifluorophenyl)-1H-pyrazol-1-yl]methyl}benzoyl)-β-alanine To a solution of the intermediate from step A in DCM (2 mL) was added TFA (2 mL). After stirring the reaction at room temperature for 1 hour, it was concentrated in vacuo and azeotroped with toluene (3×) to give the title compound. $^1$H NMR (DMSO, 500 MHz): 8.47 (t, J=5.5 Hz, 1H), 7.81 (d, J=8.9 Hz, 2H), 7.76 (d, J=8.3 Hz, 2H), 7.70 (dd, J=6.9, 8.6 Hz, 2H), 7.59 (s, 1H), 7.38 (d, J=9.0 Hz, 2H), 7.29 (d, J=8.0 Hz, 2H), 5.79 (s, 2H), 3.42 (q, J=6.9 Hz, 2H0, 2.45 (q, J=7.1 Hz, 2H). LC-MS: 2.31 min; (M+H)=607.3.

EXAMPLE 7

4-(4-{5-({[4-(TRIFLUOROMETHOXY)PHENYL]AMINO}CARBONYL)-3-(3,4,5-TRIFLUOROPHENYL)-1H-PYRAZOL-1-YL]METHYL}PHENOXY)BUTANOIC ACID

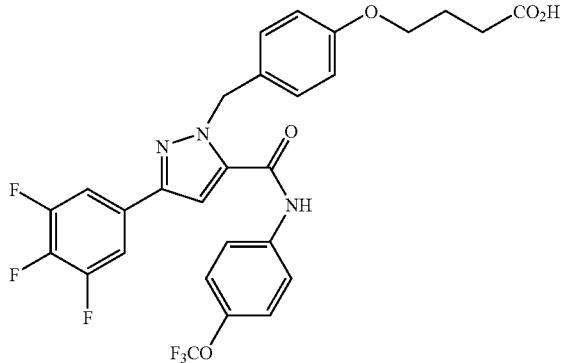

Step A. Ethyl 4-(4-formylphenoxy)butanoate

To a solution of 4-hydroxy benzaldehyde (5.0 g, 41 mmol) in anhydrous DMF (150 mL) cooled to 0° C. was added sodium hydride (1.96 g, 49.1 mmol). After 15 minutes, ethyl 4-bromobutanoate (7.02g, 49.1 mmol) was added. The cooling bath was removed and the reaction left stirring at room temperature for 18 hours. The reaction was carefully quenched by the addition of water. The resulting mixture was extracted with ethyl acetate and washed with saturated NaCl solution. The organic layer was dried over anhydrous $Na_2SO_4$ filtered and concentrated in vacuo. The residue was purified on the Biotage flash 40 M column using 10% ethyl acetate-hexanes. A colorless oil was obtained. $^1$H NMR (CDCl$_3$, 500 MHz): 9.89 (s, 1H), 7.84 (d, J=8.7 Hz, 2H), 7.01 (d, J=8.7 Hz, 2H), 4.18 (q, J=5.9 Hz, 2H), 4.1 (t, J=5.9 Hz, 2H), 2.55 (t, J=7.3 Hz, 2H), 2.17 (m, 2H), 1.28 (t, J=7.4 Hz, 2h). LC-MS=1.89 min, (M+H)=237.1.

Step B. Ethyl 4-[4-(hydroxymethyl)phenoxy]butanoate

To a solution of the intermediate form step A (8.3 g, 35.17 mmol) in methanol (200 mL) was added sodium borohydride (1.96 g, 52.7 mmol). After 2 hours the reaction mixture was concentrated in vacuo. The residue was suspended in ethyl acetate and washed with saturated NaHCO$_3$ and saturated NaCl solution. The ethyl acetate layer was dried over anhydrous Na$_2$SO$_4$ filtered and concentrated in vacuo. This material was used in the next step without any further purification. $^1$H NMR (CDCl$_3$, 500 MHz): 7.27 (d, J=8.7 Hz, 2H), 6.87 (d, J=8.4 Hz, 2H), 4.51 (s, 2H), 4.16 (q, J=7.1 Hz, 2H), 4.0 (t, J=6.0 Hz, 2H), 2.52 (t, J=7.3 Hz, 2H), 2.1 (m, 2H), 1.26 (t, J=7.1 Hz, 3H). LC-MS=2.6 min; (M+23)=261.1.

Step C. Ethyl 4-[4-(iodomethyl)phenoxy]butanoate

To a solution of the intermediate from step B (1 g, 4.24 mmol) in acetonitrile was added triphenyl phosphine (1.45 g, 5.5 mmol), imidazole (0.4 g, 5.93 mmol) and iodine (1.51 g, 5.94 mmol). After 20 minutes, the reaction was quenched with saturated Na$_2$S$_2$O$_3$ solution. The resulting mixture was extracted with ethyl acetate washed with brine and dried over anhydrous Na$_2$SO$_4$. The solution was filtered, concentrated in vacuo and purified by flash chromatography using 15% ethyl acetate-hexanes to give the desired product as an oil. $^1$H NMR (CDCl$_3$, 500 MHz): 7.32 (d, J=8.7 Hz, 2H), 6.82 (d, J=8.7 Hz, 2H), 4.48 (s, 2H), 4.18 (q, J=6.1 Hz, 2H), 4.01 (t, J=6.1 Hz, 2H), 2.53 (t, J=7.4 Hz, 2H), 2.14 (m, 2H), 1.29 (t, J=7.1 Hz, 3H). LC-MS=2.36 min; (M+23)=371.0.

Step D. 3-(3,4,5-trifluorophenyl)-1H-pyrazole-5-carboxylic acid

To a solution of the intermediate from example 1 step B (0.35 g, 1.17 mmol) in DCM (5 mL) was added TFA (5 mL). After stirring at room temperature for 2 hours, it was concentrated in vacuo and azeotroped with toluene (3×). This material was used in the next step without any further purification. $^1$H NMR (CD$_3$OD, 500 MHz): 7.59 (dd, J=6.6, 9.0 Hz, 2H), 7.18 (s, 1H). LC-MS=2.79 min; (M+H)=243.

Step E. N-[4-(trifluoromethoxy)phenyl]-3-(3,4,5-trifluorophenyl)-1H-pyrazole-5-carboxamide To a solution of the intermediate from step D (0.1 g, 0.41 mmol) in DMF (2 mL) was added 4-trifluoromethoxy aniline (83 µL, 0.61 mmol), DIEA (215 µL, 1.23 mmol), HOAt (0.08 g, 0.61 mmol) and EDC (0.118 g, 0.61 mmol). The reaction was heated at 50° C. for 3 hours. The reaction was diluted with ethyl acetate, washed with 1N HCl, saturated NaHCO$_3$, and saturated NaCl solutions. The organic layer was dried over anhydrous Na$_2$SO$_4$, filtered and concentrated in vacuo. The residue was purified by flash chromatography using 30% ethyl acetate hexanes. $^1$H NMR (DMSO, 500 MHz): 10.34 (bs, 1H), 7.93 (d, J=5.9 Hz, 2H), 7.8 (bm, 2H), 7.44 (bs, 1H), 7.37 (bd, J=8.0 Hz, 2H). LC-MS=3.76 min; (M+H)=402.

Step F. Ethyl 4-(4-{[5-{[4-(trifluoromethoxy)phenyl]amino}carbonyl)-3-(3,4,5-trifluorophenyl)-1H-pyrazol-1-yl]methyl}phenoxy)butanoate To a solution of the intermediate from step E (85 mg, 0.21 mmol) in DMF (5 mL) was added ethyl 4-[4-(iodomethyl)phenoxy]butanoate (111 mg, 0.31 mmol) followed by cesium carbonate (103 mg, 0.31 mmol). After stirring at room temperature for 2 hours the reaction was quenched by the addition of water. The resulting mixture was extracted with ethyl acetate washed with saturated NaCl solution and dried over anhydrous Na$_2$SO$_4$. The solution was filtered and concentrated in vacuo. The residue was purified by flash chromatography using 25% ethyl acetate-hexanes. $^1$H NMR (CDCl$_3$, 500 MHz): 8.78 (s, 1H), 7.74 (dd, J=2.1, 6.9 Hz, 2H), 7.25 (d, J=8.5 Hz, 2H), 6.98 (s, 1H), 6.95 (t, J=6.4 Hz, 2H), 6.85 (d, J=8.7 Hz, 2H), 5.32 (s, 2H), 4.18 (q, J=7.1 Hz, 2H), 4.03 (t, J=6.1 Hz, 2H), 2.54 (t, J=7.3 Hz, 2H), 2.15 (m, 2H), 1.29 (t, J=7.1 Hz, 3H). LC-MS: 4.42 min; (M+H)=622.2.

Step G. 4-(4-{[5-{[4-(Trifluoromethoxy)phenyl]amino}carbonyl)-3-(3,4,5-trifluorophenyl)-1H-pyrazol-1-yl]methyl}phenoxy)butanoic acid To a solution of the intermediate from step F (50 mg) in 1:1 THF/MeOH (5 mL) was added NaOH (5N, 500 µL). After stirring at room temperature for 2 hours, the reaction mixture was concentrated in vacuo. The residue was acidified with 1N HCl until the pH was less than 2. The resulting mixture was extracted with ethyl acetate, dried over anhydrous Na$_2$SO$_4$ filtered and concentrated in vacuo to give the title compound. $^1$H NMR (DMSO 500 MHz): 7.97 (d, J=7.1 Hz, 2H), 7.53 (t, J=8.2 Hz, 2H), 7.37 (d, J=8.9 Hz, 2H), 7.07 (s, 1H), 6.97 (d, J=8,7 Hz, 2H), 6.86 (d, J=8.7 Hz, 2H), 5.5 (s, 2H), 3.94 (t, J=6.4 Hz, 2H), 2.37 (t, J=7.3 Hz, 2H), 1.9 (m, 2H). LC-MS=3.95 min; (M+23)=616.1.

EXAMPLE 8

N-[(6-{[5-{[(CIS-4-TERT-BUTYLCYCLOHEXYL) AMINO]CARBONYL}-3-(3,4-DICHLOROPHE-NYL)-1H-PYRAZOL-1-YL]METHYL}PYRIDIN-3-YL)CARBONYL]-β-ALANINE

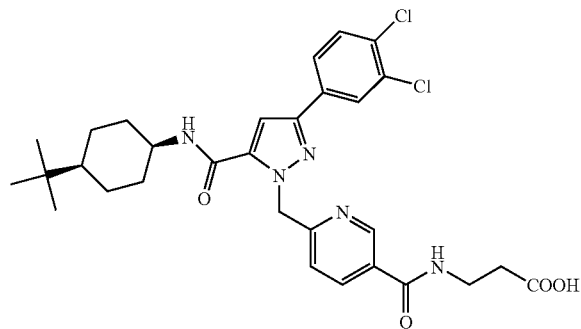

Step A. 3,4-Dichloro-N-methoxy-N-methylbenzamide

To a solution of 3,4-benzoyl chloride (5.0 g, 23.9 mmol) in DCM (200 mL) cooled to 0° C. (ice-bath) was added N,O-dimethyl-hydroxylaminehydrochloride (2.8 g, 28.6 mmol). After 10 minutes pyridine (4.25 mL, 52.5 mmol) was added to the reaction mixture, the ice-bath removed and the reaction left stirring at room temperature for 18 hours. The reaction mixture was quenched by adding water (100 mL). The resulting mixture was extracted with DCM, dried over anhydrous $Na_2SO_4$, filtered and concentrated in vacuo. The residue was purified on Biotage flash 40M column using 25% ethyl acetate-hexanes to give colorless oil. $^1$H NMR (CDCl$_3$, 500 MHz): 7.85 (d, J=1.8 Hz, 1H), 7.60 (dd, J=2.1, 8.2 Hz, 1H), 7.52 (d, J=8.4 Hz, 1H), 3.58 (s, 3H), 3.39 (s, 3H). LC-MS=2.99 min; (M+H)=234.

Step B. tert-Butyl 4-(3,4-dichlorophenyl)-4-oxobut-2-ynoate

To a solution of tert-butyl propiolate (3.72 g, 29.5 mmol) in anhydrous THF (100 mL) cooled to −78° C. under a nitrogen atmosphere, was added LHMDS (35.4 mL, 1.0 M solution, 35.4 mmol). After 5 minutes a solution of the intermediate from step A (5.75 g, 24.6 mmol) in THF (30 mL) was added to the reaction. The reaction was slowly warmed to room temperature. After 1 hour the reaction was quenched with saturated NH$_4$Cl solution. The resulting mixture was extracted with ethyl acetate (3×), washed with saturated NaCl solution and dried over anhydrous Na$_2$SO$_4$. The solution was filtered and concentrated in vacuo. The residue was purified by flash chromatography using 5% ethyl acetate-hexanes. $^1$H NMR (CDCl$_3$, 500 MHz): 8.19 (d, J=2.0 Hz, 1H), 7.98 (dd, J=2.0, 8.4 Hz, 1H), 7.64 (d, J=8.2 Hz, 1H), 1.6 (s, 9H).

Step C. tert-Butyl 3-(3,4-dichlorophenyl)-1H-pyrazole-5-carboxylate

To a solution of the intermediate from step B (4.74 g, 15.84 mmol) in DMF (30 mL) was added hydrazine (1.58 mL, 35% by wt., 17.43 mmol). After stirring the reaction at room temperature for 18 hours, it was concentrated in vacuo. The residue was suspended in ethyl acetate and washed with water (2×) and saturated NaCl solution (2×). The organic layer was dried over anhydrous MgSO$_4$ filtered and concentrated in vacuo. $^1$H NMR (CDCl$_3$, 500 MHz): 8.02 (s, 1H), 7.69 (d, J=8.2 Hz, 1H), 7.52 (d, J=8.2 Hz, 1H), 7.07 (s, 1H), 1.66 (s, 9H). LC-MS=2.52 min; (M+H−56)=257.1.

Step D. Methyl 6-(bromomethyl)nicotinate

To a solution of 6-methyl nicotinate (1.51 g, 10 mmol) in carbon tetrachloride (20 mL) was added N-bromo-succinimide (1.78 g, 10 mmol) and AIBN (164 mg, 0.1 mmol). After refluxing the reaction for 2 hours, it was diluted with carbon tetrachloride and filtered through celite. The filtrate was concentrated in vacuo and purified by flash chromatography using 15% ethyl acetate-hexanes. $^1$H NMR (CDCl$_3$, 500 MHz): 9.2 (d, J=2.0 Hz, 1H), 8.34 (dd, J=2.1, 8.0 Hz, 1H), 7.58 (d, J=8.2 Hz, 1H), 4.6 (s, 2H), 4.0 (s, 3H). LC-MS=1.71 min; (M+H)=230.0.

Step E. Methyl 6-{[5-(tert-butoxycarbonyl)-3-(3,4-dichlorophenyl)-1H-pyrazol-1-yl]methyl}nicotinate To a solution of the intermediate from step C (522 mg, 1.66 mmol) in DMF (10 mL) was added the intermediate from step D (460 mg, 2.0 mmol), followed by cesium carbonate (815 mg, 2.5 mmol). After stirring the reaction at room temperature for 3 hours, it was quenched by adding water and extracting with ethyl acetate (3×). The organic layer was washed with brine and dried over anhydrous Na$_2$SO$_4$, filtered and concentrated in vacuo. The residue was purified by flash chromatography using 30% ethyl acetate-hexanes. $^1$H NMR (CDCl$_3$, 500 MHz): 9.21 (d, J=2.1 Hz, 1H), 8.25 (dd, J=2.2, 8.2 Hz, 1H), 7.97 (d, J=1.8 Hz, 1H), 7.69 (dd, J=2.1, 8.3 Hz, 1H), 7.5 (d, J=8.2 Hz, 1H), 7.18 (s, 1H), 6.95 (d, J=8.2 Hz, 1H), 6.01 (s, 2H), 3.97 (s, 3H), 1.53 (s, 9H). LC-MS: 2.87 min; (M+H−56)=406.0.

Step F. 3-(3,4-dichlorophenyl)-1-{[5-(methoxycarbonyl)pyridin-2-yl]methyl}-1H-pyrazole-5-carboxylic acid To a solution of the intermediate from step E (551 mg, 1.19 mmol) in DCM (10 mL) was added TFA (10 mL). After stirring at room temperature for 4 hours the reaction mixture was concentrated in vacuo and azeotroped with toluene (3×). A white solid obtained. This material was used in the next step without any further purification. LC-MS: 2.38 min; (M+H)=406.0.

Step G. Methyl 6-{[5-{[(cis-4-tert-butylcyclohexyl)amino]carbonyl}-3-(3,4-dichlorophenyl)-1H-pyrazol-1-yl]methyl}nicotinate To a solution of the intermediate from step F (464 mg, 0.90 mmol) in DMF (10 mL) was added HOAt (244 mg, 1.79 mmol), tert-butyl-cyclohexylamine (426 μL, 2.39 mmol), DIEA (623 μL, 3.57 mmol) and EDC (343 mg, 1.79 mmol). The resulting slurry was left stirring at room temperature overnight. The reaction was stirred to 50° C. for 3 hours. It was cooled to room temperature, diluted with ethyl acetate, washed with 1N HCl, saturated NaHCO$_3$ solution, and dried over anhydrous Na$_2$SO$_4$. The solution was filtered and concentrated in vacuo. The residue was purified by flash chromatography using 30% ethyl acetate-hexanes. The trans and cis isomers were obtained in a 2:1 ratio. Isomer A (trans isomer): $^1$H NMR (CDCl$_3$, 500 MHz): 9.16 (d, J=1.8 Hz, 1H), 8.31 (dd, J=2.1, 8.3 Hz, 1H), 7.89 (d, J=1.9 Hz, 1H), 7.61 (dd, J=2.1, 8.5 Hz, 1H), 7.46 (d, J=8.5 Hz, 1H), 7.27 (d, J=8.2 Hz, 1H), 7.24 (d, J=7.8 Hz, 1H), 6.92 (s, 1H), 5.89 (s, 2H), 3.97 (s, 3H), 3.9 (m, 1H), 2.14 (bd, J=11.3 Hz, 2H), 1.87 (bd, J=12.6 Hz, 2H), 1.0-1.4 (m, 5H), 0.88 (s, 9H). LC-MS: 2.81 min; (M+H)=529.2. Isomer B (cis isomer): $^1$H NMR (CDCl$_3$, 500 MHz): 9.18 (d, J=2.1 Hz, 1H), 8.33 (dd, J=2.0, 8.2 Hz, 1H), 7.92 (d, J=2.0 Hz, 1H), 7.64 (dd, J=2.1, 8.3 Hz, 1H), 7.48 (d, J=8.2 Hz, 1H), 7.34 (d, J=8.0 Hz, 1H), 6.9 (s, 1H), 5.88 (s, 2H), 4.3 (m, 1H), 3.97 (s, 3H), 2.01 (d, J=13.8 Hz, 2H), 1.73 (m, 2H), 1.65 (m, 2H), 1.29 (m, 2H), 0.89 (s, 9H). LC-MS: 2.81 min; (M+H)=529.2.

Step H. 6-{[5-{[(cis-4-tert-butylcyclohexyl)amino]carbonyl}-3-(3,4-dichlorophenyl)-1H-pyrazol-1-yl]methyl}nicotinic acid To a solution of the intermediate from step G (isomer B) (0.14 g, 0.24 mmol) in 10 ml of 1:1 THF/MeOH was added 5 N NaOH (1 mL). After stirring the reaction at room temperature for 2 hours, it was concentrated in vacuo. The residue was acidified with 1N HCl (10 ml) and the resulting mixture was extracted with ethyl acetate, dried over anhydrous $Na_2SO_4$ filtered and concentrated in vacuo. This material was used in the next step without any further purification.

Step I. N-[(6-{[5-{[(cis-4-tert-butylcyclohexyl)amino]carbonyl}-3-(3,4-dichlorophenyl)-1H-pyrazol-1-yl]methyl}pyridin-3-yl)carbonyl]-β-alanine To a solution of the intermediate from step H (65 mg, 0.122 mmol) in DMF (2 mL) was added HOAt (25 mg, 0.184 mmol), β-alanine-tert-butyl ester (34 mg, 0.184 mmol), DIEA (64 μL, 0.37 mmol) and EDC (36 mg, 0.184 mmol). After stirring the reaction at room temperature for 18 hours, the reaction was diluted with ethyl acetate and washed with 1N HCl, saturated $NaHCO_3$ and saturated NaCl solution. The organic layer was dried over anhydrous $Na_2SO_4$ filtered and concentrated in vacuo. The residue was purified by flash chromatography using 30% ethyl acetate-hexanes. Colorless oil was obtained. This material was dissolved in DCM (2 mL) and TFA was added (2 mL). After 1 hour the reaction mixture was concentrated in vacuo and azeotroped with toluene (3×) to give the title compound as a solid. $^1$H NMR (DMSO, 500 MHz): 8.88 (d, J=1.4 Hz, 1H), 8.72 (t, J=5.4 Hz, 1H), 8.2 (d, J=8.7 Hz, 1H), 8.14 (dd, J=2.3, 8.2 Hz, 1H), 8.02 (d, J=1.8 Hz, 1H), 7.81 (dd, J=2.0, 8.5 Hz, 1H), 7.71 (d, J=8.4 Hz, 1H), 7.48 (s, 1H), 7.15 (d, J=8.0 Hz, 1H), 5.85 (s, 2H), 3.48 (q, J=6.9 Hz, 2H), 1.83 (bd, J=12.6 Hz, 2H), 1.45 (m, 4H), 1.25 (m, 2H), 0.98 (m, 1H), 0.83 (s, 9H). LC-MS=3.99 min, (M+H)=600.2.

EXAMPLE 9

6-{[5-{[(CIS-4-TERT-BUTYLCYCLOHEXYL) AMINO]CARBONYL}-3-(3,4-DICHLOROPHE- NYL)-1H-PYRAZOL-1-YL]METHYL}-N-1H- TETRAZOL-5-YLNICOTINAMIDE

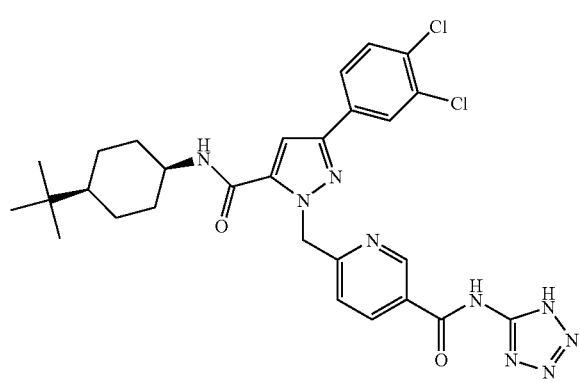

To a solution of the intermediate from example 8 step H (65 mg, 0.122 mmol) in DMF (2 mL) was added HOAt (25 mg, 0.184 mmol), amino tetrazole(32 mg, 0.36 mmol), DIEA (64 μL, 0.37 mmol) and EDC (36 mg, 0.184 mmol). The reaction was stirred at 50° C. for 18 hours. The reaction was diluted with ethyl acetate and washed with 1N HCl and saturated NaCl solution. The organic layer was dried over anhydrous $Na_2SO_4$, filtered and concentrated in vacuo. The residue was purified on the Gilson reverse phase HPLC to give the title compound. $^1$H NMR (DMSO, 500 MHz): 9.12 (s, 1H), 8.4 (dd, J=2.0, 9.1 Hz, 2H), 8.18 (d, J=6.6 Hz, 1H), 8.03 (d, J=1.9 Hz, 1H), 7.83 (dd, J=1.9, 8.3 Hz, 1H), 7.73 (d, J=8.5 Hz, 1H), 7.53 (s, 1H), 7.24 (d, J=8.2 Hz, 1H), 7.24 (d, J=8.2 Hz, 1H), 5.91 (s, 2H), 3.96 (bm, 1H), 1.83 (d, J=12.3 Hz, 2H), 1.48 (m, 3H), 1.28 (m, 2H), 0.98 (m, 1H), 0.82 (s, 9H). LC-MS=2.71 min; (M+H)=596.2.

EXAMPLE 10

N-(4-{[5-(3,4-DICHLOROPHENYL)-3-({[4-(TRIF- LUOROMETHOXY)PHENYL] AMINO}CARBONYL)-1H-PYRAZOL-1-YL] METHYL}BENZOYL)-β-ALANINE

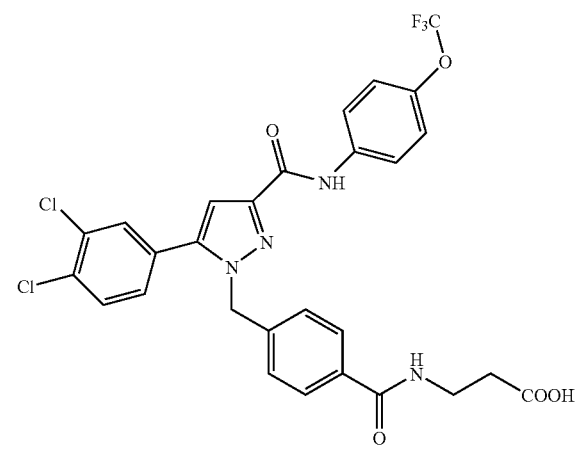

Step A. tert-butyl 4-(3,4-dichlorophenyl)-2,4-dioxobutanoate

This was prepared by following the procedure from example 1 step A. LC-MS=2.67 min; (M+H−56)=261.0

Step B. tert-butyl (2E)-2-[4-(methoxycarbonyl)benzylidene]hydrazinecarboxylate

To a solution of 4-carbomethoxy benzaldehyde (5.0 g, 36.46 mmol) in dichloroethane (40 mL) was added tert-butyl carbazate (4.03 g, 30.46 mmol) followed by AcOH (1.74 mL, 30.46 mmol). After 1.5 hours, the reaction was concentrated in vacuo. The residue was dissolved in ethyl acetate, washed with saturated $NaHCO_3$, solution, dried over anhydrous $Na_2SO_4$, filtered and concentrated in vacuo. This material was used without any further purification in the next step. $^1$H NMR ($CDCl_3$, 500 MHz): 8.03 (d, J=8.5 Hz, 3H), 7.93 (bs, 1H), 7.8 (d, J=8.2 Hz, 2H), 3.96 (s, 3H), 1.58 (s, 9H). LC-MS=3.1; (M+H−56)=223.1.

Step C. tert-Butyl 2-[4-(methoxycarbonyl)benzyl]hydrazinecarboxylate

To a solution of the intermediate from step B (8.4 g, 30.18 mmol) in THF (150 mL) was added methanol (15 mL), Na(CN)BH$_3$ (5.7 g, 90.54 mmol) and AcOH (30 mL). The resulting solution was stirred at room temperature for 48 hours. The reaction was concentrated in vacuo. To the residue was added 1 M $Na_2CO_3$ solution (800 mL) and extracted with ether (3×). The organic layer was dried over anhydrous $Na_2SO_4$ filtered and concentrated in vacuo to give the desired product as a white solid. $^1$H NMR ($CDCl_3$, 500 MHz): 8.04 (d, J=8.2 Hz, 2H), 7.46 (d, J=8.2 Hz, 2H), 4.08 (s, 2H), 3.94 (s, 3H), 1.49 (s,9H). LC-MS=2.43; (M+H−56)=224.9.

Step D. Methyl 4-(hydrazinomethyl)benzoate hydrochloride

To the intermediate from step C (1.89 g, 6.75 mmol) was added HCl (4.0 M in dioxane, 100 mL). After stirring the reaction for 16 hours it was concentrated in vacuo to give a white powder. $^1$H NMR (CD$_3$OD, 500 MHz): 8.09 (d, J=8.0 Hz, 2H), 7.57 (d, J=8.0 Hz, 2H), 4.21 (s, 2H), 3.93 (s, 3H). LC-MS=0.77; (M+H)=181.

Step E. tert-Butyl 5-(3,4-dichlorophenyl)-1-[4-(methoxycarbonyl)benzyl]-1H-pyrazole-3-carboxylate To a solution of the intermediate from step A (200 mg, 0.63 mmol) and methyl 4-(hydrazinomethyl)benzoate hydrochloride (150 mg, 0.69 mmol) in ethanol (4 mL) was added AcOH (1 mL). After stirring the reaction at room temperature for 16 hours it was concentrated in vacuo. The residue was dissolved in ethyl acetate and washed with saturated NaHCO$_3$, saturated NaCl, dried over anhydrous Na$_2$SO$_4$ filtered and concentrated in vacuo. The residue was purified by flash chromatography using 30% ethyl acetate-hexanes. (confirmed by noe experiment) $^1$H NMR (CDCl$_3$, 500 MHz): 8.0 (d, J=8.3 Hz, 2H), 7.5 (d, J=8.3 Hz, 1H), 7.37 (d, J=2.1 Hz, 1H), 7.15 (dd, J=2.1, 8.3 Hz, 1H), 7.05 (d, J=8.3 Hz, 2H), 5.5 (s, 2H), 3.95 (s, 3H), 1.6 (s, 9H). LC-MS=4.28; (M+H−56)=405.0.

N-(4-{[5-(3,4-dichlorophenyl)-3-({[4-(trifluoromethoxy)phenyl]amino}carbonyl)-1H-pyrazol-1-yl]methyl}benzoyl)-β-alanine The title compound was prepared using the procedure described in example 1 steps D-F and example 2 steps A-B. $^1$H NMR (CDCl$_3$, 500 MHz): 10.4 (s, 1H), 8.5 (bt, 1H), 7.95 (d, J=8.3 Hz, 2H), 7.8 (m, 4H), 7.4 (dd, J=2.1, 8.3 Hz, 1H), 7.35 (d, J=8.3 Hz, 2H), 7.1 (m, 3H), 5.6 (s, 2H), 3.2 (q, 2H). LC-MS=3.82; (M+H)=621.0

The following examples in Tables 1-8 can be made according to the procedures described above for Examples 1-10.

TABLE 1

| Example | R² | R¹ | LC-MS, min. (M + H) |
|---|---|---|---|
| 11 | HN-CH₂CH₂-CO₂H | Ph | 3.66 min; (M + H) = 537.1 |
| 12 | HN-tetrazole | Ph | 3.73 min; (M + H) = 533.1 |
| 13 | HN-CH₂-tetrazole | Ph | 3.63 min; (M + H) = 547.1 |
| 14 | HN-CH₂CH₂-CO₂H | 4-CF₃Ph | 3.94 min; (M + H) = 605 |
| 15 | HN-tetrazole | 4-CF₃Ph | 4.02 min; (M + H) = 601.1 |
| 16 | HN-CH₂-tetrazole | 4-CF₃Ph | 3.91 min; (M + H) = 615.1 |
| 17 | HN-CH₂CH₂-CO₂H | 3-CF₃Ph | 3.93 min; (M + H) = 605 |

TABLE 1-continued

[Structure: 3-(3,4-dichlorophenyl)-1-(4-(C(O)R²)benzyl)-1H-pyrazole-5-carboxamide with NHR¹]

| Example | R² | R¹ | LC-MS, min. (M + H) |
|---|---|---|---|
| 18 | HN-(5-amino-1H-tetrazole) | 3-CF₃Ph | 4.01 min; (M + H) = 601 |
| 19 | HN-CH₂-(1H-tetrazol-5-yl) | 3-CF₃Ph | 3.91 min; (M + H) = 615.1 |
| 20 | HN-CH₂CH₂-CO₂H | 3-CFO₃Ph | 4.02 min; (M + H) = 621 |
| 21 | HN-(5-amino-1H-tetrazole) | 3-CFO₃Ph | 4.14 min; (M + H) = 617 |
| 22 | HN-CH₂CH₂-CO₂H | trans-4-tBu-cyclohexyl | 4.26 min; (M + H) = 599.1 |
| 23 | HN-(5-amino-1H-tetrazole) | trans-4-tBu-cyclohexyl | 4.45 min; (M + H) = 595.2 |
| 24 | HN-(5-amino-1H-tetrazole) | cis-4-tBu-cyclohexyl | 4.45 min (M + H) = 595.2 |
| 25 | HN-CH₂CH₂-CO₂H | 4-CFO₃Ph | 4.0 min; (M + H) = 621.3 |
| 26 | HN-(5-amino-1H-tetrazole) | 4-CFO₃Ph | 4.2 min; (M + H) = 617.2 |
| 27 | HN-CH₂CH₂-CO₂H | 4-tBuPh | 4.15 min; (M + H) = 593.1 |
| 28 | HN-(5-amino-1H-tetrazole) | 4-tBuPh | 4.23 min; (M + H) = 589.1 |
| 29 | HN-CH₂CH₂-CO₂H | Bn | 3.65 min; (M + H) = 551.1 |

TABLE 1-continued

[Structure: 3-(3,4-dichlorophenyl)-1-(4-(C(O)R²)benzyl)-1H-pyrazole-5-carboxamide with NHR¹]

| Example | R² | R¹ | LC-MS, min. (M + H) |
|---|---|---|---|
| 30 | HN-(5-amino-1H-tetrazole) | Bn | 3.74 min; (M + H) = 547.1 |
| 31 | HN-(5-amino-1H-tetrazole) | ᵗBu | 3.77 min; (M + H) = 513.1 |
| 32 | HN-(5-amino-1H-tetrazole) | CF₃CH₂ | 3.62 min; (M + H) = 539.1 |
| 33 | HN-CH₂CH₂-CO₂H | 2-indanyl | 3.8 min; (M + H) = 577.1 |
| 34 | HN-(5-amino-1H-tetrazole) | 2-indanyl | 3.9 min; (M + H) = 573.3 |
| 35 | HN-CH₂CH₂-CO₂H | 4-FPh | 3.74 min; (M + H) = 555 |
| 36 | HN-(5-amino-1H-tetrazole) | 4-FPh | 3.84 min; (M + H) = 551.1 |
| 37 | HN-CH₂CH₂-CO₂H | 3,4-diFPh | 3.83 min; (M + H) = 573.1 |
| 38 | HN-(5-amino-1H-tetrazole) | 3,4-diFPh | 3.91 min; (M + H) = 569.1 |
| 39 | HN-CH₂CH₂-CO₂H | 4-cHexylPh | 4.36 min; (M + H) = 619.1 |
| 40 | HN-CH₂CH₂-CO₂H | 1-phenylethyl | 3.71 min; (M + H) = 565.1 |

TABLE 1-continued

| Example | R² | R¹ | LC-MS, min. (M + H) |
|---|---|---|---|
| 41 | HN-tetrazole | 1-phenylethyl | 3.81 min; (M + H) = 561.1 |
| 42 | HN-CH₂CH₂-CO₂H | 1-phenylethyl | 3.71 min; (M + H) = 565.1 |
| 43 | HN-tetrazole | 1-phenylethyl | 3.81 min; (M + H) = 561.1 |
| 44 | HN-CH₂CH₂-CO₂H | 1-phenylcyclopropyl | 3.7 min; (M + H) = 577.1 |
| 45 | HN-tetrazole | 1-phenylcyclopropyl | 3.81 min; (M + H) = 573.1 |
| 46 | HN-tetrazole | 2-(pyridin-2-yl)propan-2-yl | 3.91 min; (M + H) = 575.1 |
| 47 | HN-CH₂CH₂-CO₂H | 3-MeOPh | 3.74 min; (M + H) = 567.1 |
| 48 | HN-tetrazole | 3-MeOPh | 3.82 min; (M + H) = 563.1 |
| 49 | HN-CH₂CH₂-CO₂H | 4-MeOPh | 3.68 min; (M + H) = 567.1 |

TABLE 1-continued

| Example | R² | R¹ | LC-MS, min. (M + H) |
|---|---|---|---|
| 50 | HN-tetrazol-5-yl | 4-MeOPh | 3.78 min; (M + H) = 563.1 |
| 51 | HN-CH₂CH₂-CO₂H | 4-methylthiazol-2-yl | 3.52 min; (M + H) = 558.1 |
| 52 | HN-CH₂CH₂-CO₂H | 5-methylthiazol-2-yl | 2.24 min; (M + H) = 558.1 |
| 53 | HN-CH₂CH₂-CO₂H | 4,5-dimethylthiazol-2-yl | 2.29 min; (M + H) = 572.1 |
| 54 | HN-tetrazol-5-yl | 5-methylpyridin-2-yl | 2.05 min; (M + H) = 548 |
| 55 | HN-CH₂CH₂-CO₂H | 5-methylpyridin-2-yl | 2.2 min; (M + H) = 552.1 |
| 56 | HN-tetrazol-5-yl | 1-phenylpiperidin-4-yl | 2.11 min; (M + H) = 616.2 |
| 57 | HN-CH₂CH₂-CO₂H | 1-phenylpiperidin-4-yl | 2.04 min; (M + H) = 620.2 |
| 58 | HN-tetrazol-5-yl | 4-phenylcyclohexyl | 4.41 min; (M + H) = 615.2 |

TABLE 1-continued

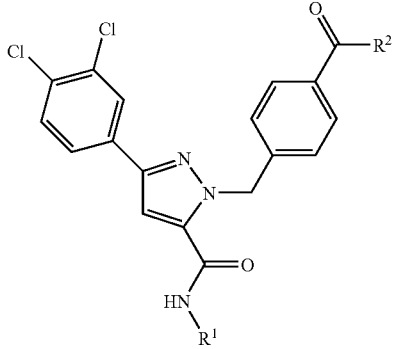

| Example | R² | R¹ | LC-MS, min. (M + H) |
|---|---|---|---|
| 59 | HN-CH₂CH₂-CO₂H | 4-Ph-cyclohexyl | 4.04 min; (M + H) = 619.1 |
| 60 | HN-tetrazole | 4-cHexylPh | 4.38 min; (M + H) = 615.2 |
| 61 | HN-CH₂CH₂-CO₂H | 4-tBu-cyclohexyl | 4.23 min; (M + H) = 599.2 |

TABLE 2

| Example | R² | R¹ | LC-MS, min. (M + H) |
|---|---|---|---|
| 62 | 4-CF₃O | 4-FPh | 3.65 min; (M + H) = 571.1 |
| 63 | 4-CF₃O | 4-CF₃OPh | 3.89 min; (M + H) = 637.1 |
| 64 | 3,5-diF | 4-FPh | 3.49 min; (M + H) = 523.1 |
| 65 | 3,5-diF | 4-CF₃OPh | 3.77 min (M + H) = 589.1 |
| 66 | 3,4-diF | 4-FPh | 3.46 min; (M + H) = 523.1 |
| 67 | 3,4-diF | 4-CF₃OPh | 3.95 min; (M + H) = 567.2 |

TABLE 2-continued

| Example | R² | R¹ | LC-MS, min. (M + H) |
|---|---|---|---|
| 68 | 4-CF₃O | 4-tBu-cyclohexyl | 4.13 min; (M + H) = 615.2 |
| 69 | 3,5-diF | 4-tBu-cyclohexyl | 3.95 min; (M + H) = 567.2 |

TABLE 2-continued

[Structure: pyrazole with R2-phenyl group, N-benzyl with para-C(O)NH-CH2CH2-CO2H, and C(O)NH-R1]

| Example | R² | R¹ | LC-MS, min. (M + H) |
|---|---|---|---|
| 70 | 3,4-diF | (trans-4-tert-butylcyclohexyl) | 3.95 min; (M + H) = 567.2 |
| 71 | 3,4-diF | (cis-4-tert-butylcyclohexyl) | 3.96 min; (M + H) = 567.3 |
| 72 | 2,4,5-triF | (trans-4-tert-butylcyclohexyl) | 2.44 min; (M + H) = 585.3 |
| 73 | 2,4,5-triF | 4-CF₃OPh | 2.3 min; (M + H) = 607.3 |
| 74 | 3,5-diCl | 4-CF₃OPh | 3.97 min; (M + H) = 621.1 |

TABLE 3

[Structure: pyrazole with R-phenyl group, N-benzyl with para-C(O)NH-tetrazole, and C(O)NH-R1]

| Example | R² | R¹ | LC-MS, min. (M + H) |
|---|---|---|---|
| 75 | 4-CF₃O | 4-FPh | 3.75 min; (M + H) = 567.4 |
| 76 | 4-CF₃O | 4-CF₃OPh | 3.99; (M + H) = 633.4 |
| 77 | 3,5-diF | 4-CF₃OPh | 4.9 min; (M + H) = 585.1 |
| 78 | 3,4-diF | 4-CF₃OPh | 4.91 min; (M + H) = 585.4 |
| 79 | 4-CF₃O | (trans-4-tert-butylcyclohexyl) | 4.19 min; (M + H) = 611.2 |
| 80 | 4-CF₃O | (cis-4-tert-butylcyclohexyl) | 4.18 min; (M + H) = 611.2 |
| 81 | 3,5-diF | (trans-4-tert-butylcyclohexyl) | 4.07 min; (M + H) = 563.2 |
| 82 | 3,5-diF | (cis-4-tert-butylcyclohexyl) | 4.06 min; (M + H) = 563.2 |
| 83 | 3,4-diF | (trans-4-tert-butylcyclohexyl) | 4.03 min; (M + H) = 563.2 |
| 84 | 3,4-diF | (cis-4-tert-butylcyclohexyl) | 4.02 min; (M + H) = 563.2 |
| 85 | 2,4,5-triF | (trans-4-tert-butylcyclohexyl) | 4.03 min; (M + H) = 581.2 |
| 86 | 2,4,5-triF | (cis-4-tert-butylcyclohexyl) | 4.07 min; (M + H) = 581.2 |
| 87 | 2,4,5-triF | 4-CF₃OPh | 3.86 min; (M + H) = 603.1 |
| 88 | 3,5-diCl | 4-CF₃OPh | 4.1 min; (M + H) = 617.1 |

TABLE 4
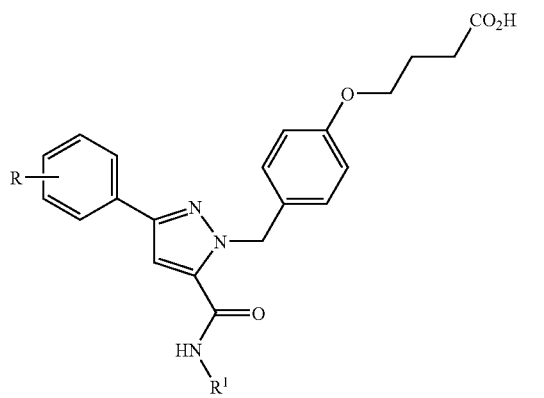
| Example | R² | R¹ | LC-MS, min. (M + H) |
|---|---|---|---|
| 89 | 3,4-diCl | 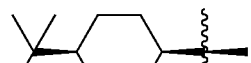 | 4.51 min; (M + H) = 486.1 |
| 90 | 3,4-diF | 4-CF₃OPh | 4.52 min; (M + H) = 604.2 |
| 91 | 3,5-diF | 4-CF₃OPh | 4.2 min; (M + H) = 604.2 |
| 92 | 3,5-diF | 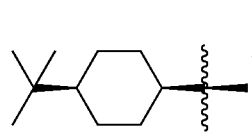 | 2.59 min; (M + H) = 576.3 |
TABLE 5
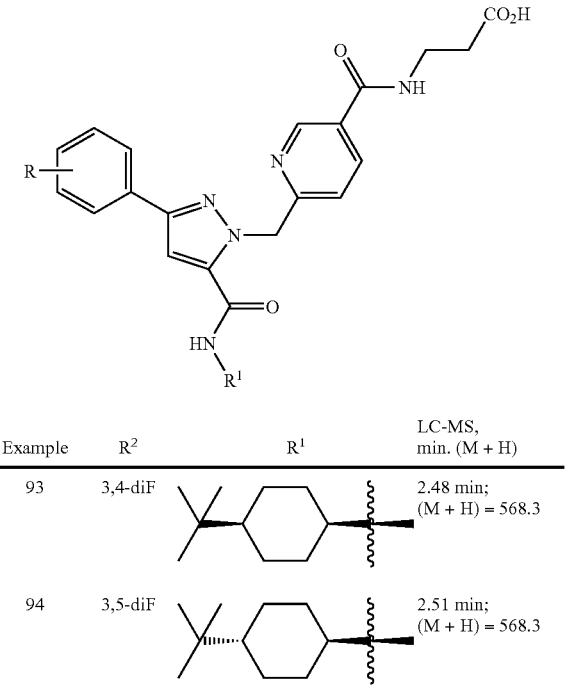
| Example | R² | R¹ | LC-MS, min. (M + H) |
|---|---|---|---|
| 93 | 3,4-diF | | 2.48 min; (M + H) = 568.3 |
| 94 | 3,5-diF | | 2.51 min; (M + H) = 568.3 |
TABLE 5-continued
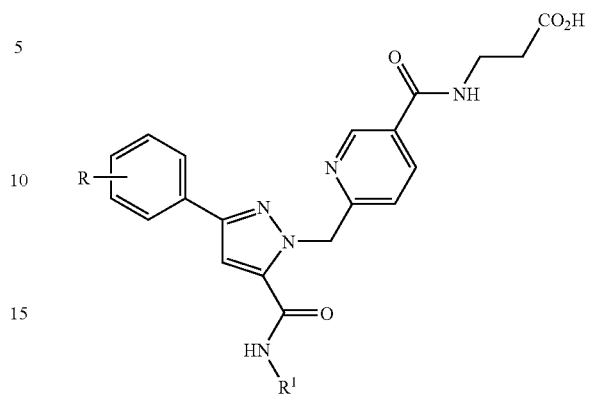
| Example | R² | R¹ | LC-MS, min. (M + H) |
|---|---|---|---|
| 95 | 3,5-diF | | 2.50 min; (M + H) = 568.3 |
TABLE 6
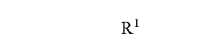
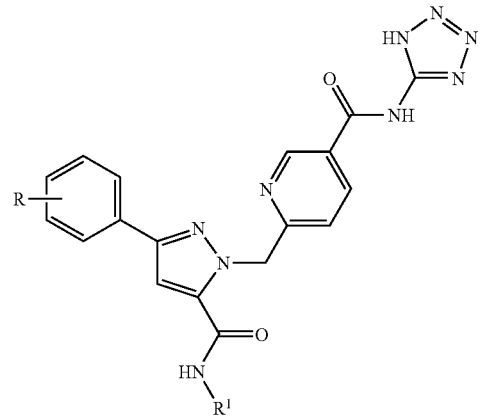
| Example | R² | R¹ | LC-MS, min. (M + H) |
|---|---|---|---|
| 96 | 3,4-diCl | | 2.71 min; (M + H) = 596.2 |
| 97 | 3,4-diCl | | 2.71 min; (M + H) = 596.2 |
| 98 | 3,4-diF | | 3.87 min; (M + H) = 564.3 |
| 99 | 3,4-diF | | 3.89 min; (M + H) = 564.4 |

TABLE 6-continued

[Structure: R-phenyl-pyrazole with pyridine-carboxamide-tetrazole and C(O)NHR¹ substituent]

| Example | R² | R¹ | LC-MS, min. (M + H) |
|---|---|---|---|
| 100 | 3,5-diF | [trans-4-tBu-cyclohexyl] | 3.82 min; (M + H) = 564.3 |
| 101 | 3,5-diF | [cis-4-tBu-cyclohexyl] | 3.83 min; (M + H) = 564.3 |

TABLE 7

[Structure: R-phenyl-pyrazole with benzyl-C(O)NH-CH2CH2CO2H and C(O)NHR¹ substituent]

| Example | R² | R¹ | LC-MS, min. (M + H) and NMR |
|---|---|---|---|
| 102 | 3,4-diCl | Ph | 3.48 min; (M + H) = 537.1 |
| 103 | 3,4-diCl | 3-CF₃Ph | 3.79 min; (M + H) = 605.1 |
| 104 | 3,4-diCl | 4-CF₃Ph | 3.81 min; (M + H) = 605.1 |
| 105 | 3,4-diCl | 3-CF₃OPh | 3.85 min; (M + H) = 621.1 |
| 106 | 3,4-diCl | 4-CF₃OPh | 3.8 min; (M + H) = 621 |
| 107 | 3,4-diCl | 4-tBuPh | 3.93 min; (M + H) = 593.1 |
| 108 | 3,4-diCl | [trans-4-tBu-cyclohexyl] | 3.96 min (M + H) = 599.2 |
| 109 | 4-CF₃O | 4-CF₃OPh | 3.79 min; (M + H) = 637 |

TABLE 7-continued

[Structure: same as Table 7]

| Example | R² | R¹ | LC-MS, min. (M + H) and NMR |
|---|---|---|---|
| 110 | 4-CF₃O | [trans-4-tBu-cyclohexyl] | 3.93 min; (M + H) = 615 |
| 111 | 4-CF₃O | [cis-4-tBu-cyclohexyl] | 3.93 min; (M + H) = 615 |

TABLE 8

[Structure: R-phenyl-pyrazole with benzyl-C(O)NH-tetrazole and C(O)NHR¹ substituent]

| Example | R² | R¹ | LC-MS, min. (M + H) |
|---|---|---|---|
| 112 | 3,4-diCl | Ph | 3.58 min; (M + H) = 533.1 |
| 113 | 3,4-diCl | 3-CF₃Ph | 3.87 min; (M + H) = 601.1 |
| 114 | 3,4-diCl | 4-CF₃Ph | 3.88 min; (M + H) = 601.1 |
| 115 | 3,4-diCl | 4-tBuPh | 4.01 min; (M + H) = 589.1 |
| 116 | 3,4-diCl | [trans-4-tBu-cyclohexyl] | 4.05 min; (M + H) = 595.2 |
| 117 | 3,4-diCl | [cis-4-tBu-cyclohexyl] | 4.07 min; (M + H) = 595.2 |
| 118 | 4-CF₃O | 4-CF₃OPh | 3.78 min; (M + H) = 633 |

TABLE 8-continued

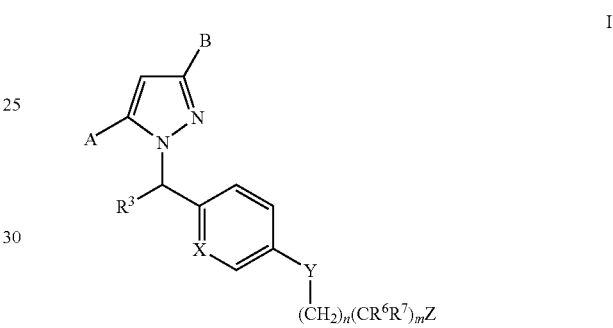

| Example | R² | R¹ | LC-MS, min. (M + H) |
|---|---|---|---|
| 119 | 4-CF₃O | | 3.93 min; (M + H) = 611 |
| 120 | 4-CF₃O | | 3.92 min; (M + H) = 611 |

BIOLOGICAL ASSAYS

The ability of the compounds of the present invention to inhibit the binding of glucagon and their utility in treating or preventing type 2 diabetes mellitus and the related conditions can be demonstrated by the following in vitro assays. *Glucagon Receptor Binding Assay*

A stable CHO (Chinese hamster ovary) cell line expressing cloned human glucagon receptor was maintained as described (Chicchi et al. *J Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/− compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. The $IC_{50}$ values were calculated using non-linear regression analysis assuming single site competition. $IC_{50}$ values for the compounds of the invention are generally in the range of as low as about 1 nM to as high as about 500 nM, and thus have utility as glucagon antagonists.

Inhibition of Glucagon-stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound represented by formula I:

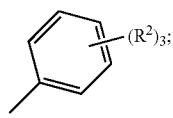

or a pharmaceutically acceptable salt or solvate thereof, wherein:
Y represents —C(O)—N(R⁵)— or —O—;
one of A and B represents —C(O)—NH—R¹ and the other represents $R^1$ represents H or is independently selected from the group consisting of:
a) $C_{1-16}$alkyl optionally substituted with:
  (1) 1-5 halo groups up to a perhaloalkyl group;
  (2) 1 oxo group;
  (3) 1-2 OH groups;
  (4) 1-2 $C_{1-10}$alkoxy groups, each optionally substituted with:
    up to five halo or a perhaloalkoxy, 1 OH or $CO_2R^a$ group;
  (5) 1 $CO_2R^a$ or $S(O)_pR^d$;
  (6) 1-2 Aryl, Hetcy or HAR groups, each optionally substituted as follows:
    (a) 1-5 halo groups,
    (b) 1 OH, $CO_2R^a$, CN, $S(O)_pR^d$, $NO_2$ or $C(O)NR^bR^c$,
    (c) 1-2 $C_{1-10}$alkyl or alkoxy groups, each optionally substituted with: 1-5 halo, up to perhaloalkyl, and 1-2 OH or $CO_2R^a$ groups; and
  (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups;
b) Aryl, HAR, Hetcy, each optionally substituted as set forth below:
(1) 1-3 $C_{1-10}$alkyl or alkoxy groups optionally substituted as follows: 1-5 halo groups; 1-2 OH groups; $CO_2R^a$; CN; $S(O)_pR^d$; phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and
(2) phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups;
said Aryl, HAR, Hetcy group b) being further optionally substituted on carbon by a group selected from the group consisting of;
(3) 1-5 halo groups;
(4) 1-2 OH groups;
(5) 1 $S(O)_pR^d$, $NO_2$ or CN group;
(6) 1-2 $CO_2R^a$;
(7) —$C(O)NR^bR^c$;
each $R^2$ is H or is selected from the group consisting of:
(a) halo, OH, $CO_2R^a$, CN, $SO_pR^d$, $NO_2$,
(b) $C_{1-6}$alkyl or $OC_{1-6}$alkyl optionally substituted with: (1) 1-5 halo groups up to a perhaloalkyl group; (2) $CO_2R^a$ CN, $S(O)_pR^d$ or OH; (3) phenyl optionally substituted as follows: (i) 1-5 halo groups, (ii) 1 $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups;
$R^3$ is H or $C_{1-3}$alkyl;
$R^5$ is H or $C_{1-6}$alkyl;
$R^6$ is selected from the group consisting of H, OH, F and $C_{1-3}$alkyl;
$R^7$ is H or F, or $R^6$ and $R^7$ are taken in combination and represent oxo;
$R^a$ is H or $C_{1-10}$alkyl, optionally substituted with phenyl, OH, $OC_{1-6}$alkyl, $CO_2H$, $CO_2C_{1-6}$alkyl and 1-3 halo groups;
$R^b$ is H or $C_{1-10}$alkyl;
$R^c$ is H or is independently selected from:
(a) $C_{1-10}$alkyl, optionally substituted with OH, $OC_{1-6}$alkyl, $CO_2H$, $CO_2C_{1-6}$alkyl, and 1-3 halo groups;
(b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo;
(c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and
(d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;
$R^d$ is $C_{1-10}$alkyl, Aryl or Ar—$C_{1-10}$ alkyl;
m is an integer selected from 0, 1 and 2;
n is an integer selected from 0 to 6;
p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl) and
X is CH or N.
2. A compound in accordance with claim 1 wherein:
Y represents —$C(O)$—$N(R^5)$— or —O—;
one of A and B represents —$C(O)$—NH—$R^1$ and the other represents

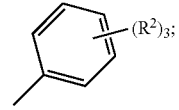

$R^1$ represents H or is independently selected from the group consisting of:
a) $C_{1-10}$alkyl optionally substituted with:
(1) 1-3 halo groups;
(2) 1 oxo group;
(3) 1 OH groups;
(4) 1-2 $C_{1-4}$alkoxy groups, each optionally substituted with:
up to three halo groups;
(5) 1 $CO_2R^a$ or $S(O)_pR^d$;
(6) 1 Aryl, Hetcy or HAR group, optionally substituted as follows:
(a) 1-3 halo groups,
(b) 1 $CO_2R^a$, CN, $S(O)_pR^d$, $NO_2$ or $C(O)NR^bR^c$,
(c) 1-$C_{1-6}$alkyl or alkoxy group, each optionally substituted with: 1-3 halo groups; and
(d) 1 phenyl ring, optionally substituted as follows: 1-3 halo groups, 1-2 $C_{1-3}$alkyl or alkoxy groups, each being further optionally substituted with 1-3 halo groups;
b) Aryl, HAR, Hetcy, each optionally substituted as set forth below:
(1) 1-2 $C_{1-6}$alkyl or alkoxy groups optionally substituted as follows: 1-3 halo groups; OH, $CO_2R^a$; CN; $S(O)_pR$; phenyl optionally substituted as follows: (i) 1-3 halo groups, (ii) 1 $CO_2R^a$, CN, $S(O)_pR^d$, $NO_2$ or $C(O)NR^bR^c$ group, (iii) 1-2 $C_{1-6}$alkyl or alkoxy groups, each optionally substituted with: 1-3 halo, and 1-2 OH or $CO_2R^a$ groups; and
(2) phenyl optionally substituted as follows: (i) 1-3 halo groups, (ii) 1 $CO_2R^a$, CN, $S(O)_pR^d$, $NO_2$ or $C(O)NR^bR^c$ group, (iii) 1-2 $C_{1-6}$alkyl or alkoxy groups, each optionally substituted with: 1-3 halo groups;
said Aryl, HAR, Hetcy group b) being further optionally substituted on carbon by a group selected from the group consisting of;
(3) 1-3 halo groups;
(4) 1 OH, $S(O)_pR^d$, $NO_2$, CN, $CO_2R^a$ or —$C(O)NR^bR^c$ group;
each $R^2$ is H or is selected from the group consisting of:
(a) halo, $CO_2R^a$, CN, $SO_pR^d$, $NO_2$,
(b) $C_{1-6}$alkyl or $OC_{1-6}$alkyl optionally substituted with: (1) 1-3 halo groups up to a perhaloalkyl group; (2) $CO_2R^a$ CN, $S(O)_pR$ or OH; (3) phenyl optionally substituted as follows: (i) 1-3 halo groups, (ii) 1 $CO_2R^a$, CN, $S(O)_pR$, $NO_2$ or $C(O)NR^bR^c$ group, (iii) 1-2 $C_{1-6}$alkyl or alkoxy groups, each optionally substituted with: 1-5 halo groups;
$R^3$ and $R^5$ are H or $C_{1-3}$ alkyl;
$R^6$ is selected from the group consisting of H, OH, F and $C_{1-3}$alkyl;
$R^7$ is H or F;

R$^a$ is H or C$_{1-6}$alkyl, optionally substituted with phenyl, OH, OC$_{1-4}$alkyl, CO$_2$H, CO$_2$C$_{1-6}$alkyl and 1-3 halo groups;

R$^b$ is H or C$_{1-3}$alkyl;

R$^c$ is H or is independently selected from:

(a) C$_{1-6}$alkyl, optionally substituted with OH, OC$_{1-4}$alkyl, CO$_2$H, CO$_2$C$_{1-6}$alkyl, and 1-3 halo groups;

(b) Aryl or Ar—C$_{1-6}$alkyl, each optionally substituted with 1-3 halos and 1 member selected from the group consisting of: CN, OH, C$_{1-6}$alkyl and OC$_{1-6}$ alkyl, said alkyl and alkoxy being further optionally substituted with 1-3 halo groups up to perhalo;

(c) Hetcy or Hetcy-C$_{1-6}$alkyl, optionally substituted with 1-3 halo groups and 1 group selected from: oxo, C$_{1-6}$alkyl and OC$_{1-6}$ alkyl, said alkyl and alkoxy being further optionally substituted with 1-3 halo groups up to perhalo; and (d) HAR or HAR-C$_{1-6}$alkyl, optionally substituted with 1-5 halo groups and 1 group selected from: C$_{1-6}$alkyl and OC$_{1-6}$ alkyl, said alkyl and alkoxy being further optionally substituted with 1-3 halo groups up to perhalo;

R$^d$ is C$_{1-6}$alkyl, Aryl or Ar—C$_{1-6}$alkyl;

m is an integer selected from 0, 1 and 2;

n is an integer selected from 0 to 6;

p is an integer selected from 0, 1 and 2, and when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl) and X is CH or N.

3. A compound in accordance with claim 1 wherein: Y represents —C(O)—NR$^5$—.

4. A compound in accordance with claim 1 wherein A represents —C(O)NH—R$^1$.

5. A compound in accordance with claim 1 wherein Y represents O.

6. A compound in accordance with claim 5 wherein R$^5$ represents H.

7. A compound in accordance with claim 1 wherein B represents —C(O)NH—R$^1$.

8. A compound in accordance with claim 6 wherein R$^1$ represents H, C$_{1-10}$alkyl, or aryl optionally substituted with C$_{1-6}$alkyl, OC$_{1-6}$alkyl, haloC$_{1-6}$alkyl and haloC$_{1-6}$alkoxy.

9. A compound in accordance with claim 1 wherein each R$^2$ is independently selected from the group consisting of: H, halo, C$_{1-6}$alkyl and OC$_{1-6}$alkyl.

10. A compound in accordance with claim 1 wherein X represents CH.

11. A compound in accordance with claim 1 wherein m and n represent 0, 1 or 2, such that the sum of m and n is 0, 1, 2 or 3.

12. A compound in accordance with claim 1 wherein Z represents tetrazole or CO$_2$H.

13. A compound in accordance with claim 1 wherein:

X represents CH;

Y represents —C(O)—NH—;

A represents —C(O)NH—R$^1$ wherein R$^1$ represents a member selected from the group consisting of: H, C$_{1-10}$alkyl, aryl-C$_{1-6}$alkyl or aryl optionally substituted with one of C$_{1-6}$alkyl, OC$_{1-6}$alkyl, haloC$_{1-6}$alkyl and haloC$_{1-6}$alkoxy;

B represents

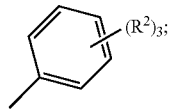

each R$^2$ is independently selected from the group consisting of: H, halo, C$_{1-6}$alkyl and OC$_{1-6}$alky;

R$^3$ represents H;

n and m represent 0, 1 or 2, such that the sum of m and n is 0, 1, 2 or 3 and

Z represents tetrazole or CO$_2$H.

14. A compound in accordance with claim 1 selected from the following tables:

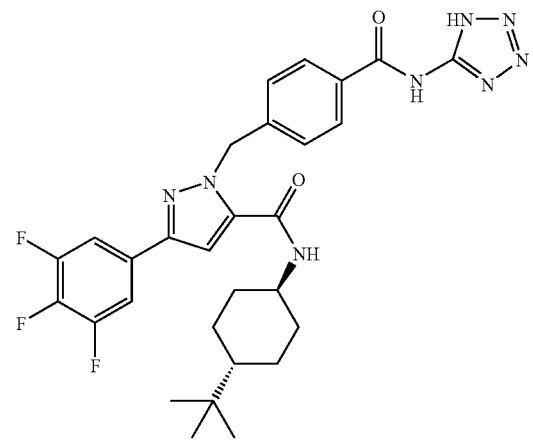

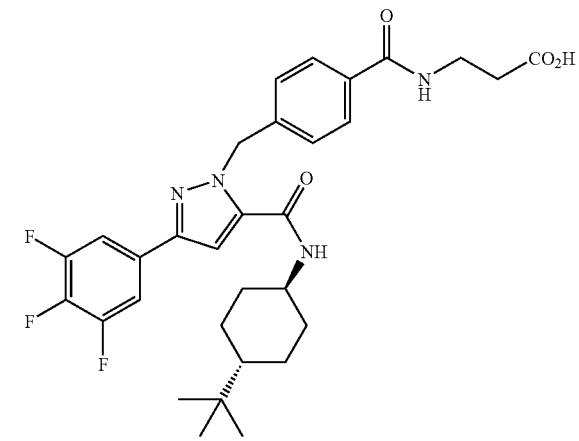

-continued
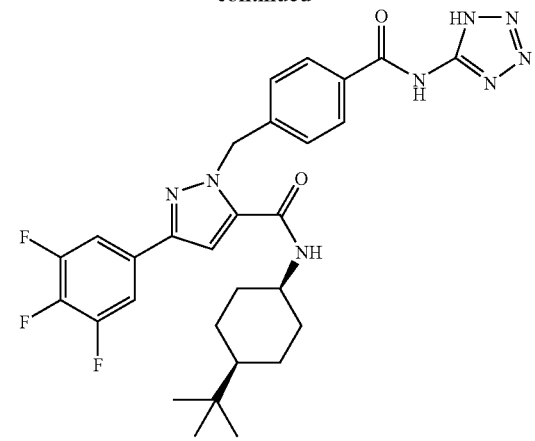
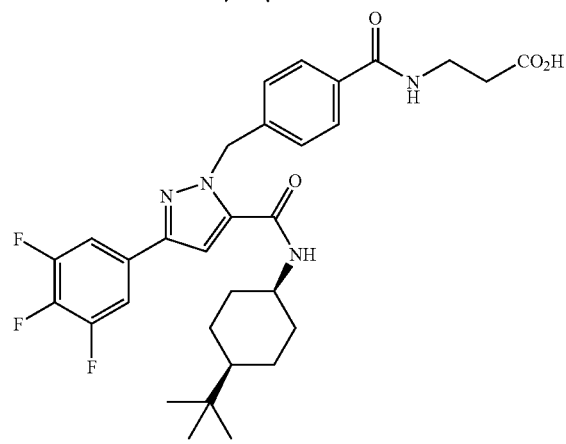
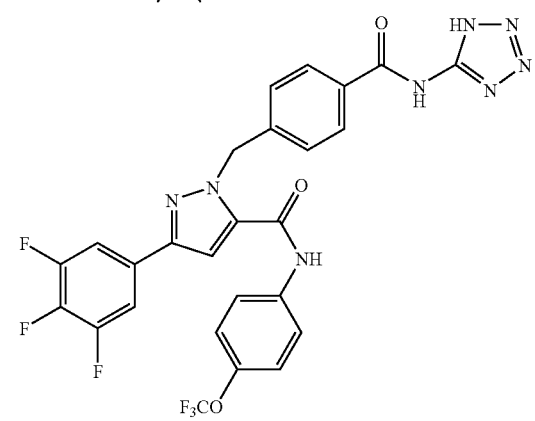
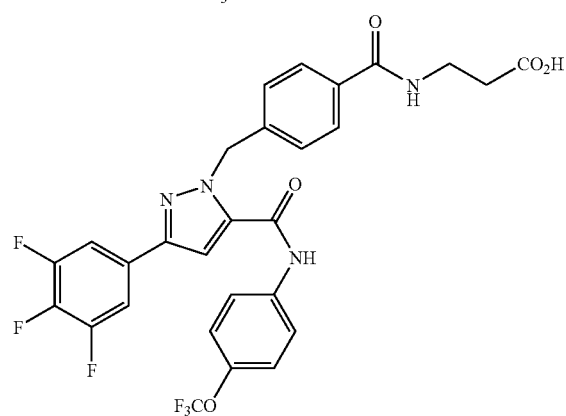
-continued
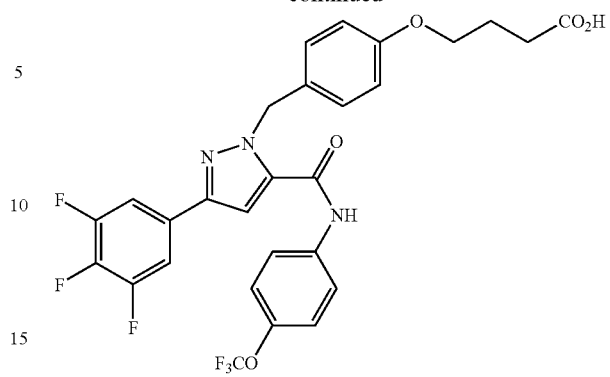
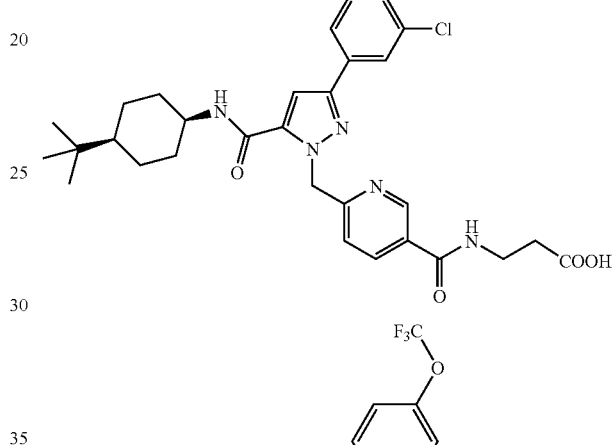
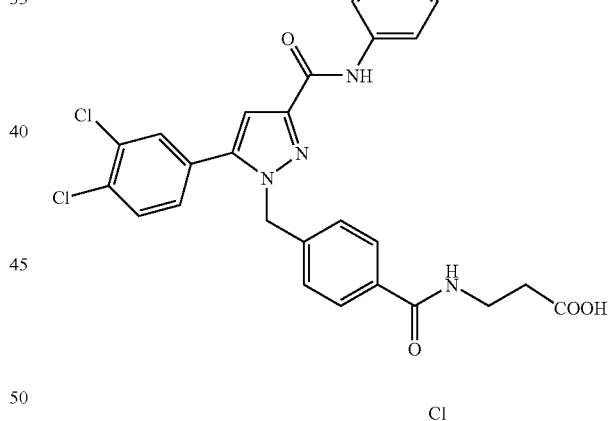
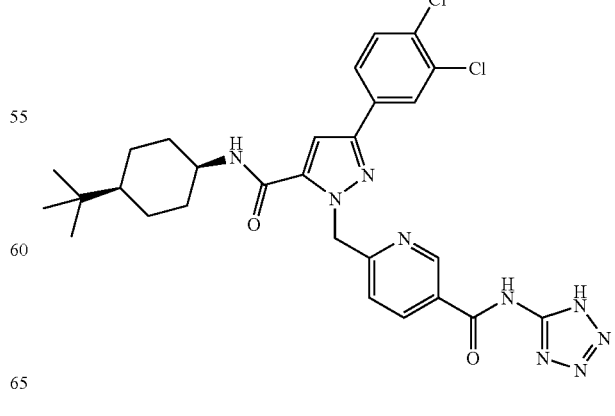

TABLE 1
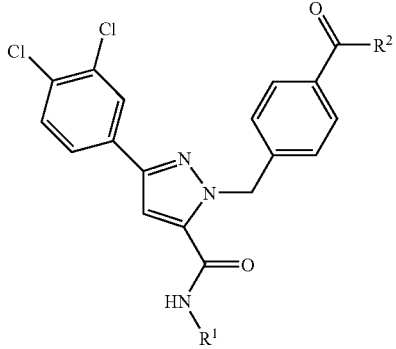
| R² | R¹ |
|---|---|
|  | Ph |
|  | Ph |
|  | 4-CF₃Ph |
|  | 3-CF₃Ph |
|  | 3-CF₃Ph |
|  | 3-CFO₃Ph |
|  | 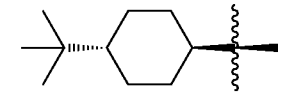 |
|  | 4-CFO₃Ph |
|  | 4-ᵗBuPh |
|  | Bn |
|  | ᵗBu |
|  | 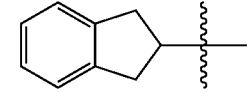 |
|  | 4-FPh |
TABLE 1-continued
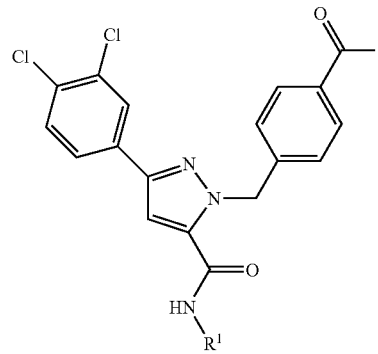
| R² | R¹ |
|---|---|
|  | 3,4-diFPh |
| 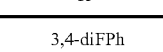 | 4-cHexylPh |
|  | 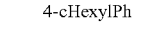 |
|  | 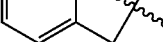 |
| 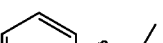 |  |
|  | 3-MeOPh |
| 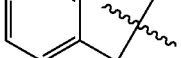 | 4-MeOPh |
|  |  |
|  |  |
|  | 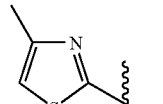 |

TABLE 1-continued
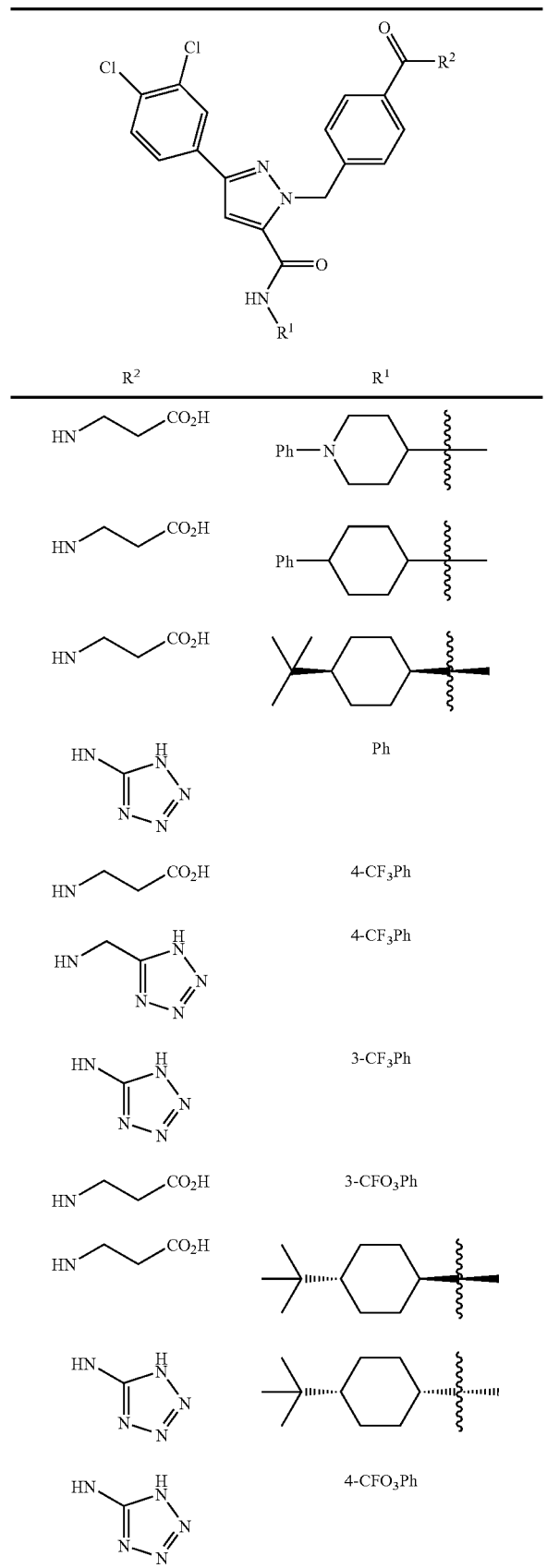
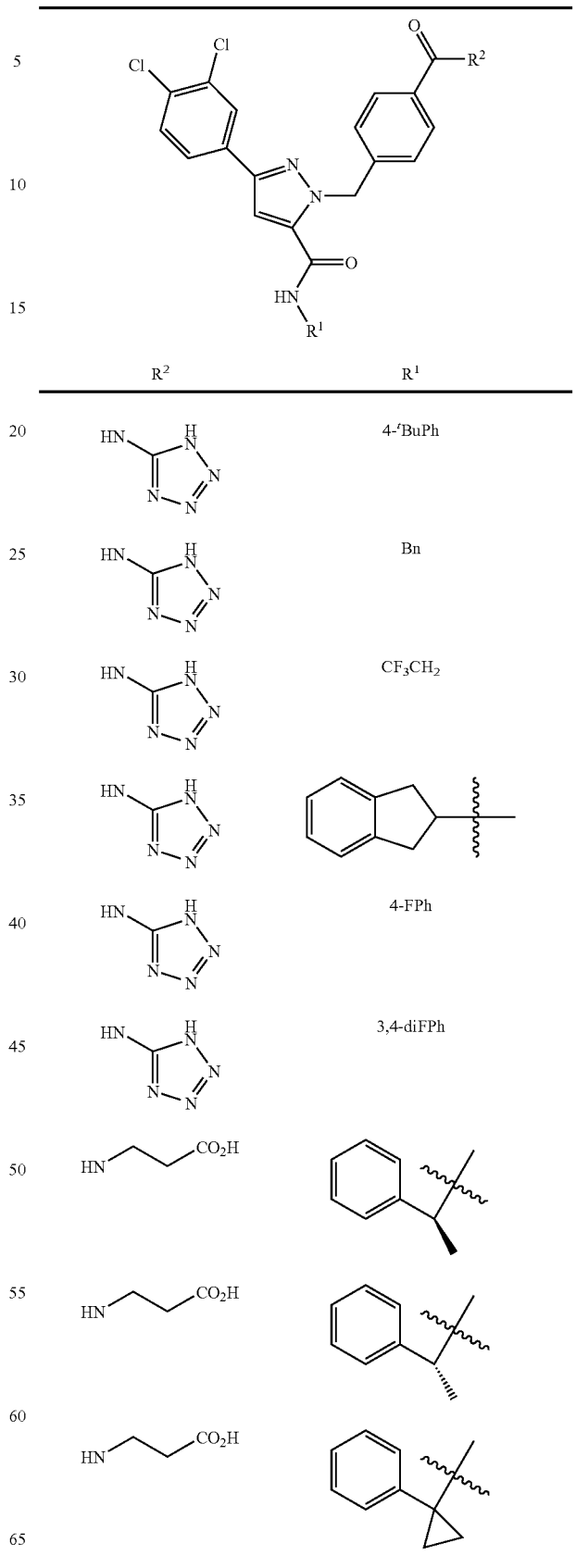

TABLE 1-continued
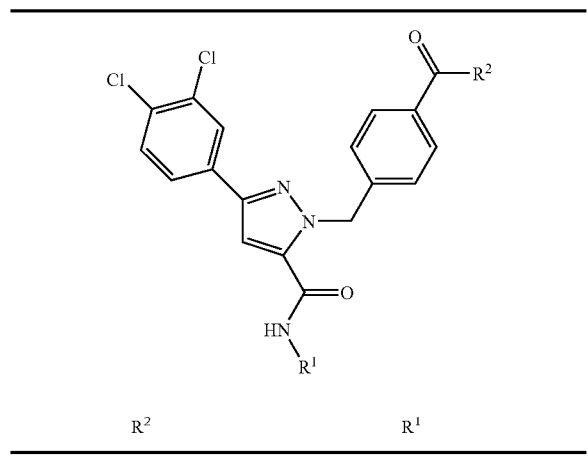
| R² | R¹ |
|---|---|
| 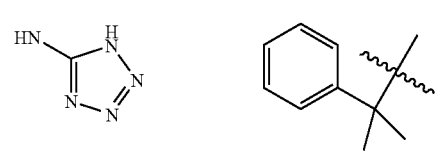 | 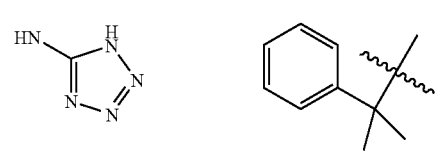 |
|  | 3-MeOPh |
|  | 4-MeOPh |
| 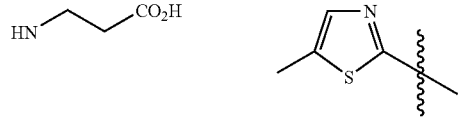 | 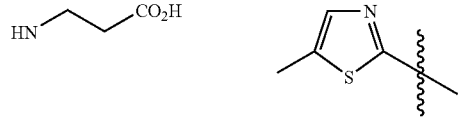 |
| 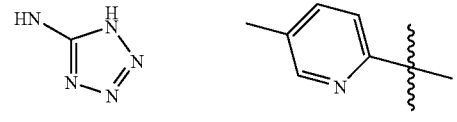 | 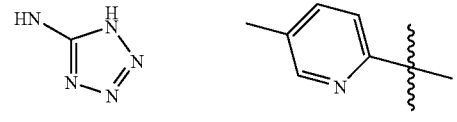 |
| 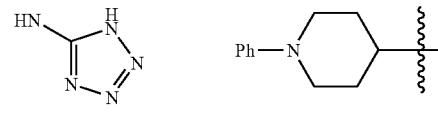 | 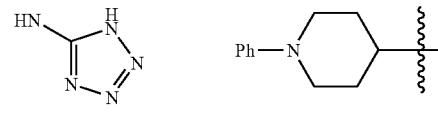 |
| 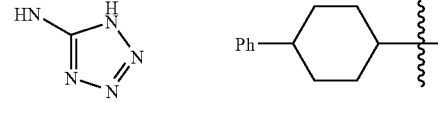 | 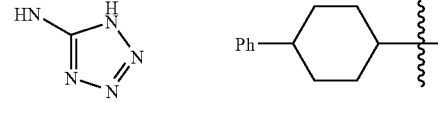 |
|  | 4-cHexylPh |
TABLE 2
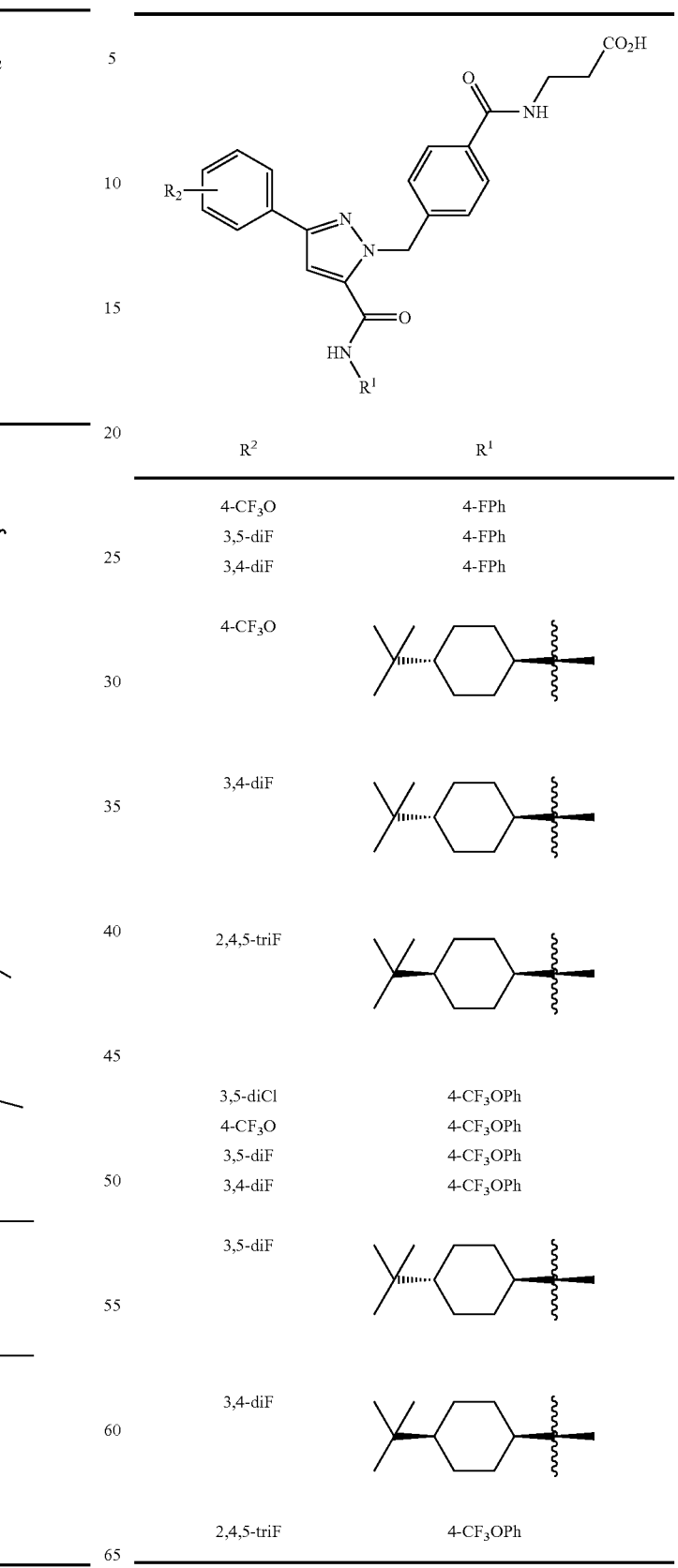
| R² | R¹ |
|---|---|
| 4-CF₃O | 4-FPh |
| 3,5-diF | 4-FPh |
| 3,4-diF | 4-FPh |
| 4-CF₃O | 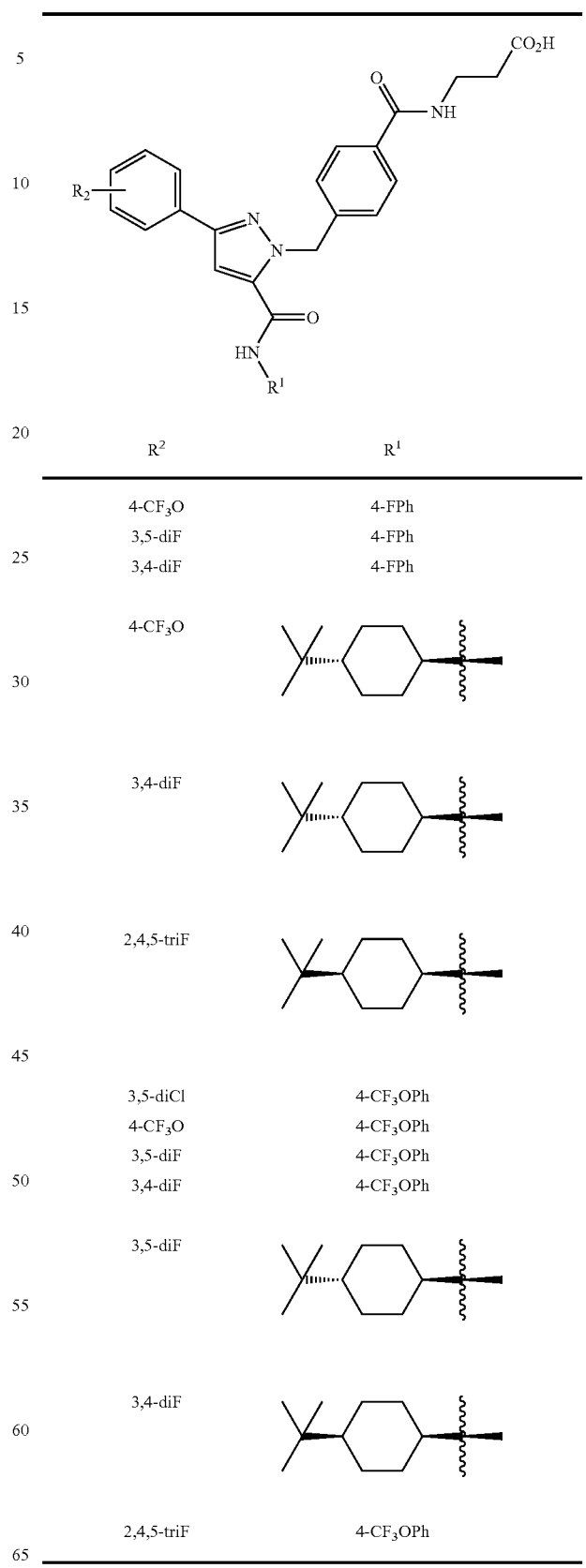 |
| 3,4-diF | 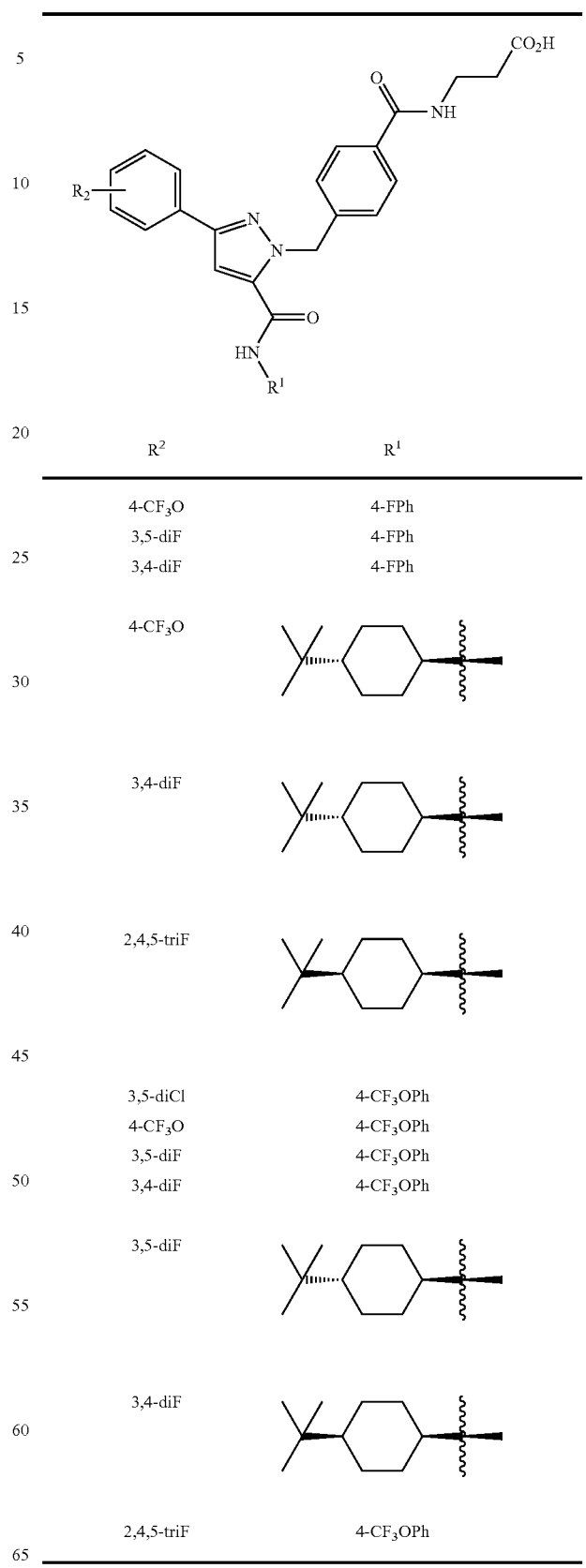 |
| 2,4,5-triF | 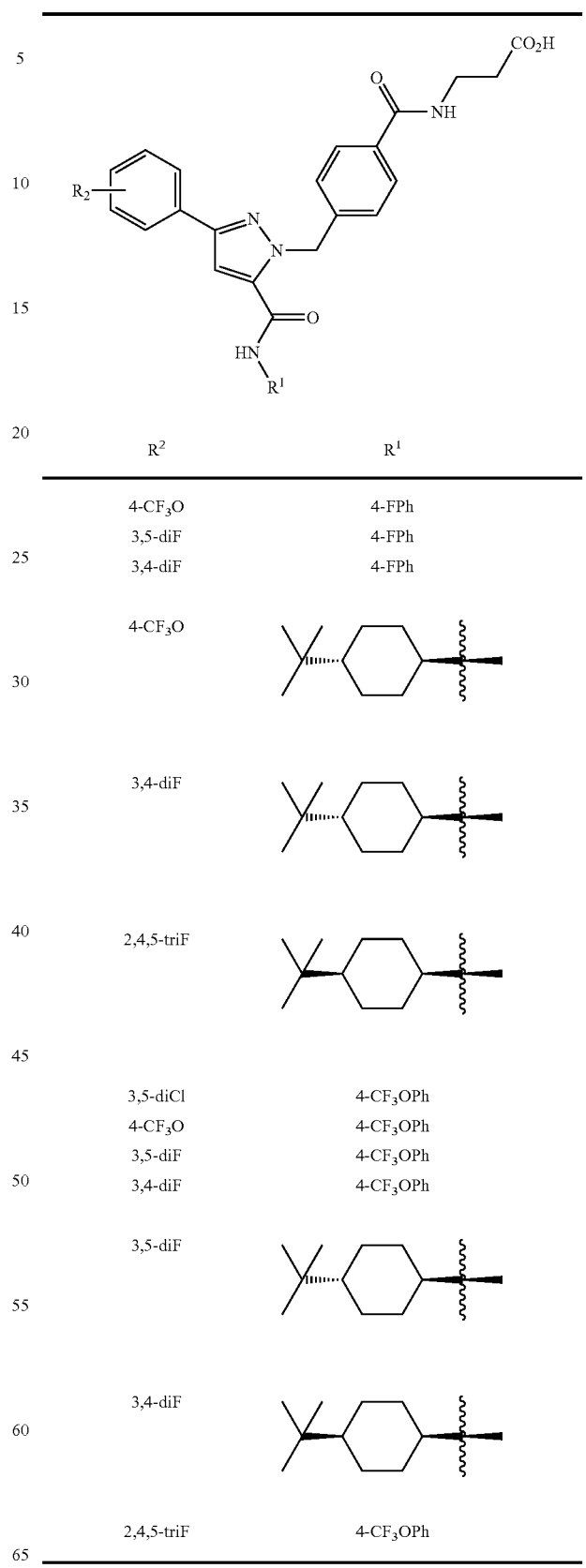 |
| 3,5-diCl | 4-CF₃OPh |
| 4-CF₃O | 4-CF₃OPh |
| 3,5-diF | 4-CF₃OPh |
| 3,4-diF | 4-CF₃OPh |
| 3,5-diF | 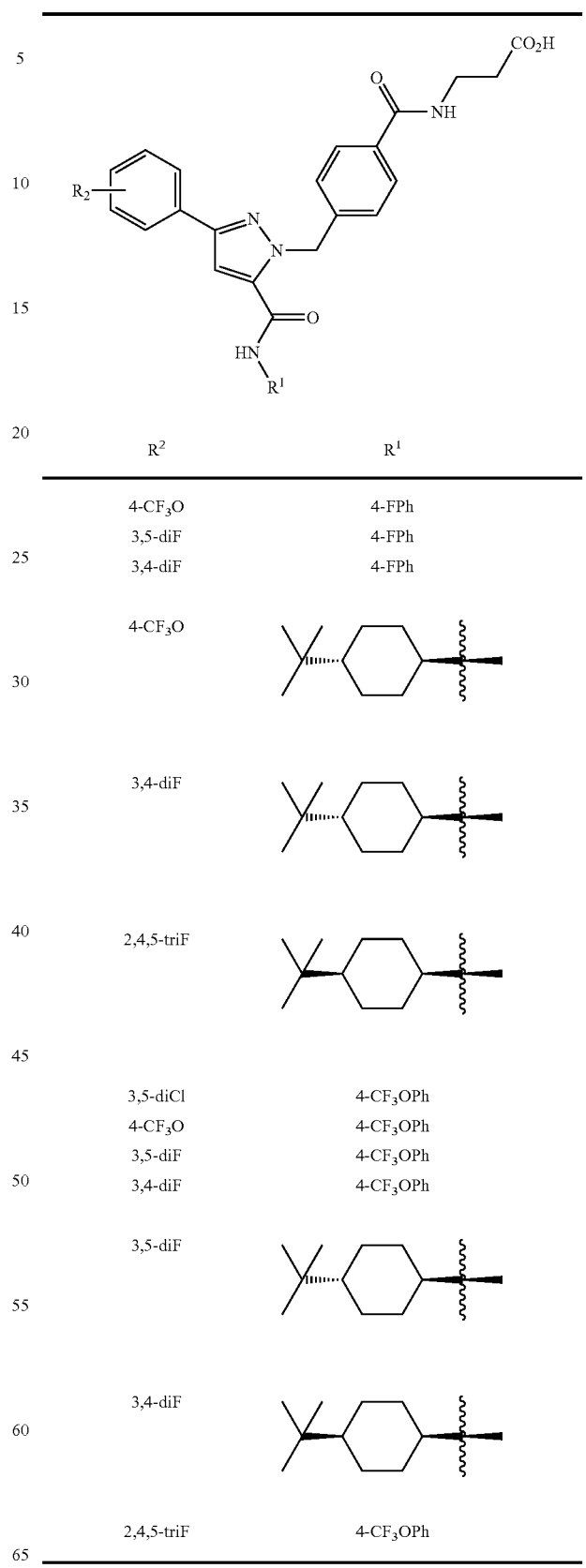 |
| 3,4-diF | 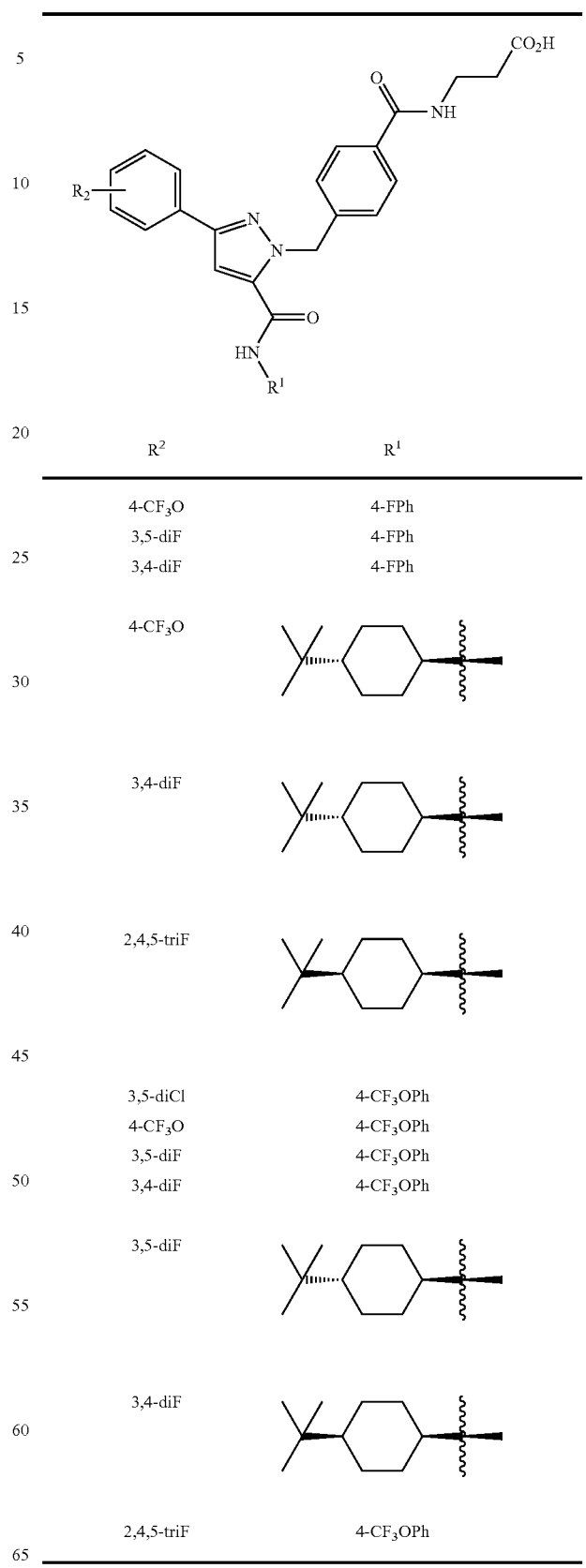 |
| 2,4,5-triF | 4-CF₃OPh |

TABLE 3

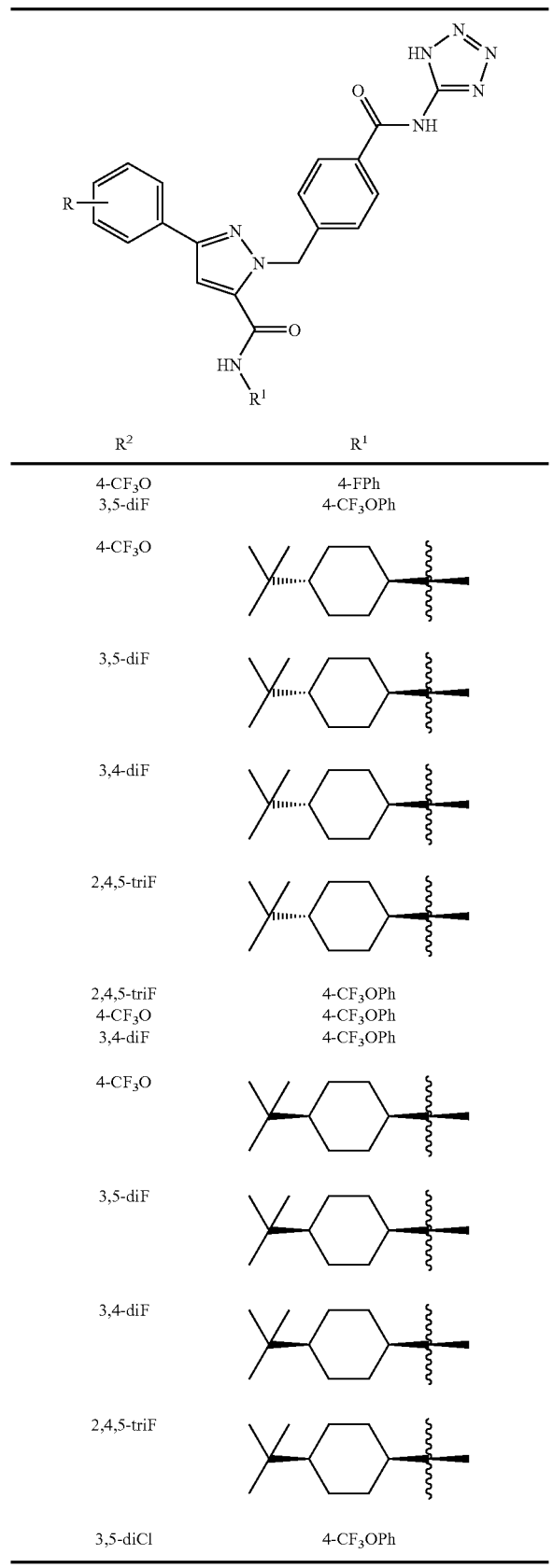

| R² | R¹ |
|---|---|
| 4-CF₃O | 4-FPh |
| 3,5-diF | 4-CF₃OPh |
| 4-CF₃O | *tBu-cyclohexyl* |
| 3,5-diF | *tBu-cyclohexyl* |
| 3,4-diF | *tBu-cyclohexyl* |
| 2,4,5-triF | *tBu-cyclohexyl* |
| 2,4,5-triF | 4-CF₃OPh |
| 4-CF₃O | 4-CF₃OPh |
| 3,4-diF | 4-CF₃OPh |
| 4-CF₃O | *tBu-cyclohexyl* |
| 3,5-diF | *tBu-cyclohexyl* |
| 3,4-diF | *tBu-cyclohexyl* |
| 2,4,5-triF | *tBu-cyclohexyl* |
| 3,5-diCl | 4-CF₃OPh |

TABLE 4

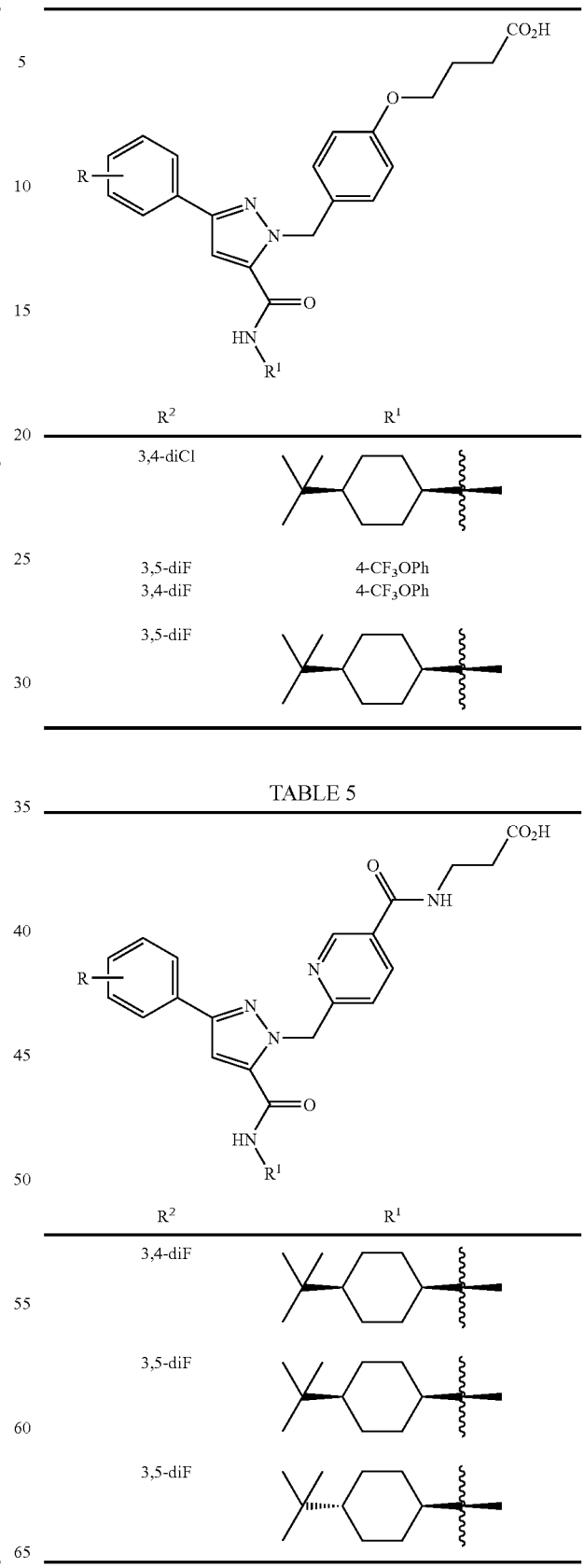

| R² | R¹ |
|---|---|
| 3,4-diCl | *tBu-cyclohexyl* |
| 3,5-diF | 4-CF₃OPh |
| 3,4-diF | 4-CF₃OPh |
| 3,5-diF | *tBu-cyclohexyl* |

TABLE 5

| R² | R¹ |
|---|---|
| 3,4-diF | *tBu-cyclohexyl* |
| 3,5-diF | *tBu-cyclohexyl* |
| 3,5-diF | *tBu-cyclohexyl* |

TABLE 6

| $R^2$ | $R^1$ |
|---|---|
| 3,4-diCl | 4-tBu-cyclohexyl |
| 3,4-diF | 4-tBu-cyclohexyl |
| 3,5-diF | 4-tBu-cyclohexyl |
| 3,4-diCl | 4-tBu-cyclohexyl |
| 3,4-diF | 4-tBu-cyclohexyl |
| 3,5-diF | 4-tBu-cyclohexyl |

TABLE 7

| $R^2$ | $R^1$ |
|---|---|
| 3,4-diCl | Ph |
| 3,4-diCl | 4-CF$_3$Ph |
| 3,4-diCl | 4-CF$_3$OPh |
| 3,4-diCl | 4-tBu-cyclohexyl |
| 4-CF$_3$O | 4-tBu-cyclohexyl |
| 3,4-diCl | 3-CF$_3$Ph |
| 3,4-diCl | 3-CF$_3$OPh |
| 3,4-diCl | 4-tBuPh |
| 4-CF$_3$O | 4-CF$_3$OPh |
| 4-CF$_3$O | 4-tBu-cyclohexyl |

TABLE 8

| $R^2$ | $R^1$ |
|---|---|
| 3,4-diCl | Ph |
| 3,4-diCl | 4-CF$_3$Ph |
| 3,4-diCl | 4-tBu-cyclohexyl |
| 4-CF$_3$O | 4-CF$_3$OPh |
| 4-CF$_3$O | 4-tBu-cyclohexyl |

TABLE 8-continued

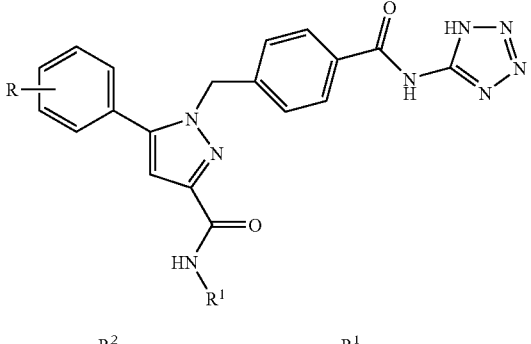

| R² | R¹ |
|---|---|
| 3,4-diCl | 3-CF₃Ph |
| 3,4-diCl | 4-ᵗBuPh |
| 3,4-diCl | 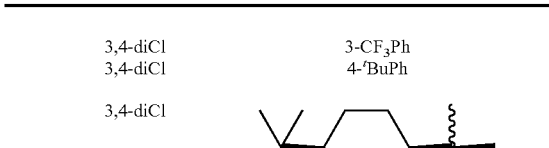 |
| 4-CF₃O | 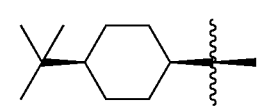 | or a pharmaceutically acceptable salt or solvate thereof.

15. A pharmaceutical composition comprising a compound in accordance with claim 1 in combination with a pharmaceutically acceptable carrier.

16. A method of treating type 2 diabetes mellitus in a mammalian patient in need of such treatment comprising administering to said patient a compound in accordance with claim 1 in an amount that is effective to treat said type 2 diabetes mellitus.

17. A method of delaying the onset of type 2 diabetes mellitus in a mammalian patient in need thereof, comprising administering to the patient a compound in accordance with claim I in an amount that is effective to delay the onset of said type 2 diabetes mellitus.

18. A method of treating hyperglycemia, diabetes or insulin resistance in a mammalian patient in need of such treatment which comprises administering to said patient an effective amount of a compound in accordance with claim 1.

19. A method of treating non-insulin dependent diabetes mellitus in a mammalian patient in need of such treatment comprising administering to the patient an anti-diabetic effective amount of a compound in accordance with claim 1.

20. A method of treating obesity in a mammalian patient in need of such treatment comprising administering to said patient a compound in accordance with claim 1 in an amount that is effective to treat obesity.

21. A method of treating Syndrome X in a mammalian patient in need of such treatment, comprising administering to said patient a compound in accordance with claim 1 in an amount that is effective to treat Syndrome X.

22. A method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with claim 1 in an amount that is effective to treat said lipid disorder.

23. A method of treating atherosclerosis in a mammalian patient in need of such treatment, comprising administering to said patient a compound in accordance with claim 1 in an amount effective to treat atherosclerosis.

\* \* \* \* \*